United States Patent
Alekseenko et al.

(10) Patent No.: US 12,297,490 B2
(45) Date of Patent: May 13, 2025

(54) METHODS FOR ASYMMETRIC DNA LIBRARY GENERATION AND OPTIONALLY INTEGRATED DUPLEX SEQUENCING

(71) Applicant: SOPHIA GENETICS S.A., Saint-Sulpice (CH)

(72) Inventors: Alisa Alekseenko, Saint-Sulpice (CH); Vicente Jose Pelechano Garcia, Saint-Sulpice (CH)

(73) Assignee: SOPHIA GENETICS S.A., Rolle (CH)

( * ) Notice: Subject to any disclaimer, the term of this patent is extended or adjusted under 35 U.S.C. 154(b) by 1114 days.

(21) Appl. No.: 17/271,815

(22) PCT Filed: Aug. 28, 2019

(86) PCT No.: PCT/EP2019/073019
§ 371 (c)(1),
(2) Date: Feb. 26, 2021

(87) PCT Pub. No.: WO2020/043803
PCT Pub. Date: Mar. 5, 2020

(65) Prior Publication Data
US 2021/0317517 A1    Oct. 14, 2021

Related U.S. Application Data

(60) Provisional application No. 62/723,719, filed on Aug. 28, 2018.

(51) Int. Cl.
| | | |
|---|---|---|
| *C12Q 1/6855* | (2018.01) | |
| *C12N 15/10* | (2006.01) | |
| *C12Q 1/6806* | (2018.01) | |

(52) U.S. Cl.
CPC ....... *C12Q 1/6855* (2013.01); *C12N 15/1068* (2013.01); *C12Q 1/6806* (2013.01)

(58) Field of Classification Search
CPC .......... C12Q 1/6855; C12N 15/1068
See application file for complete search history.

(56) References Cited

U.S. PATENT DOCUMENTS

| | | |
|---|---|---|
| 7,985,565 B2 | 7/2011 | Mayer et al. |
| 9,910,956 B2 | 3/2018 | Travers et al. |
| 2016/0319345 A1 | 11/2016 | Gnerre et al. |
| 2017/0211140 A1 | 7/2017 | Schmitt et al. |
| 2018/0223350 A1 * | 8/2018 | Galvin ............... C12N 15/1065 |

FOREIGN PATENT DOCUMENTS

| | | | |
|---|---|---|---|
| WO | 2010/048605 | 4/2010 | |
| WO | WO-2013142389 A1 * | 9/2013 | ........... C12Q 1/6806 |
| WO | 2015/106890 | 7/2015 | |
| WO | 2018/144159 | 8/2018 | |

OTHER PUBLICATIONS

International Search Report issued in PCT/EP2019/073019, mailed Jan. 2, 2020.
Written Opinion of the International Searching Authority issued in PCT/EP2019/073019, mailed Jan. 2, 2020.

* cited by examiner

*Primary Examiner* — Juliet C Switzer
*Assistant Examiner* — Jill Leigh Hudacek
(74) *Attorney, Agent, or Firm* — Bochner PLLC; Andrew Bochner; Eric Kleinertz

(57) ABSTRACT

Methods and products are disclosed for asymmetrically adapting fragmented nucleic acids for next generation sequencing, including providing strand identifier sequences and index sequences to identify the source strand and sample, respectively, of the fragmented nucleic acids. The methods and products allow for efficient and reliable detection of low-frequency mutations including in subpopulations of cells within a subject and also for the amplification of the fragmented nucleic acids when there is a low yield of isolated fragmented nucleic acids.

11 Claims, 11 Drawing Sheets

Specification includes a Sequence Listing.

Figure 1
Adaptor containing strand identifier sequence (SIS)
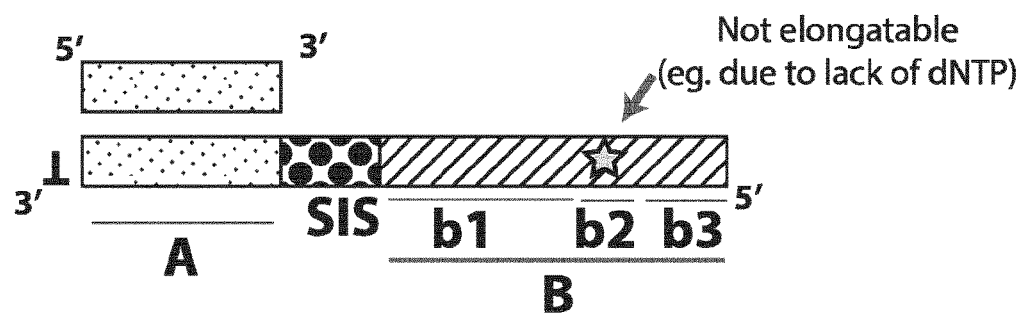
First Primering Sequence (PS-1)
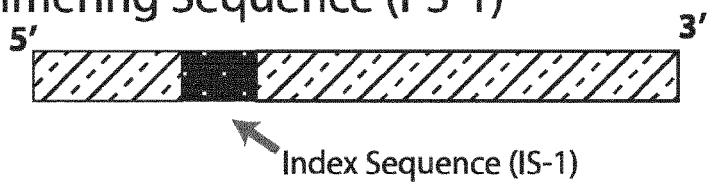
SecondPrimering Sequence (PS-2)
Blocking oligo
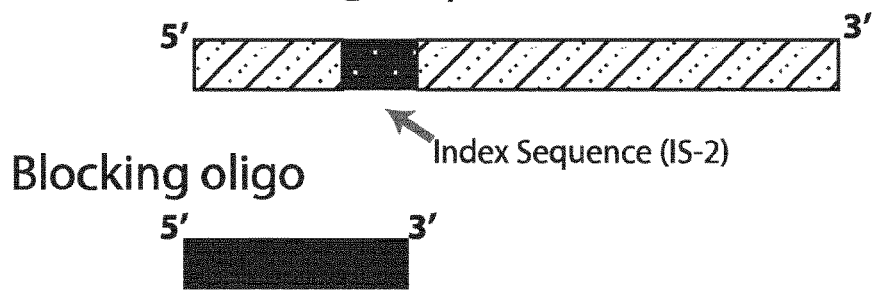

Figure 2

Step 1. Ligation of adaptors

Step 2. Add reaction mix 1
- PCR enzyme buffer with dNTPs (no dTTP, or other dNTP)
- PS-1 oligo and blocking oligo
- Incubate 10 seconds at 72°C (do not denature)

2.1 Adaptor elongates copying SIS but not reaching the end

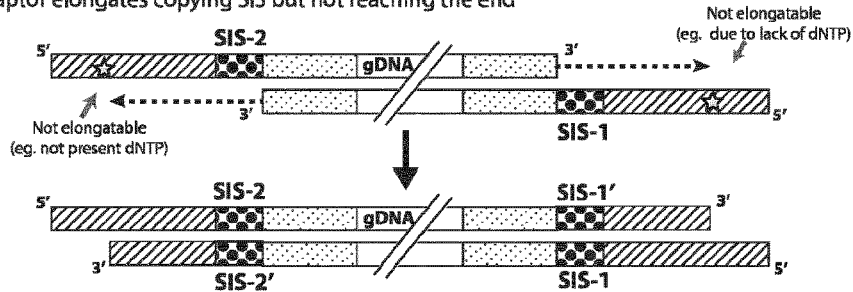

2.2 Denaturation and annealing of PS-1 and blocking oligo. Elongation starts.
-Denature and incubate 60 seconds at 48°C. (Only one strand is shown)

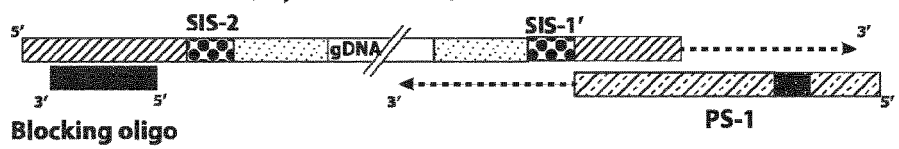

Step 3. Add reaction mix 2
- Mix 2 contains dTTP (or other lacking dNTP) and oligo PS-2
- Incubate at 48°C for 30 seconds (optional) and 30 seconds at 72°C to displace blocking oligo and finish elongation of PS-1

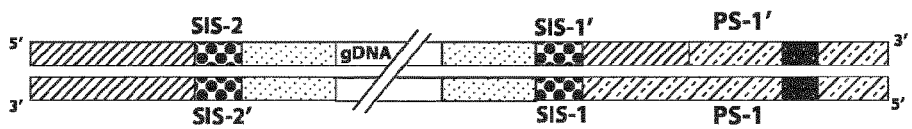

3.1 Denaturation and annealing to elongate PS-2 and PS-1
- Denature and anneal at 60°C to elongate PS-2. Only the strand binding PS-2 is shown.
The other strand will be incorparated in the second cycle of the PCR

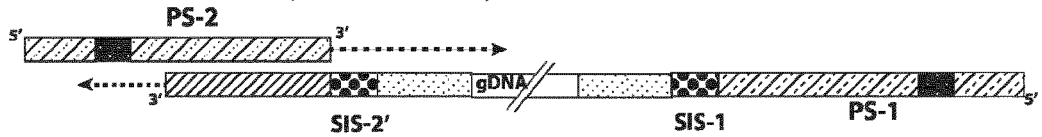

3.2 Proceed with regular PCR reaction. Please note asymmetry.

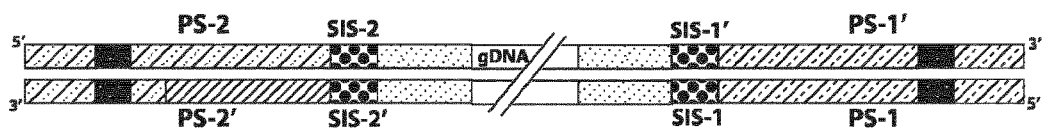

Step 4. Proceed to target enrichment and/or sequencing

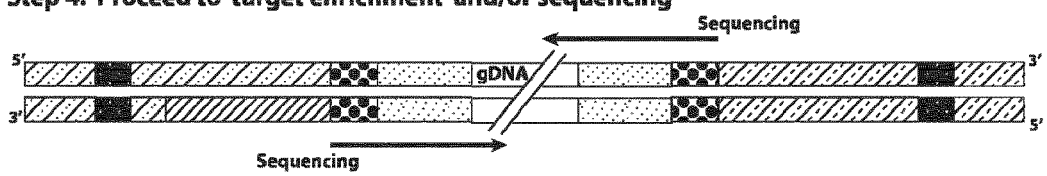

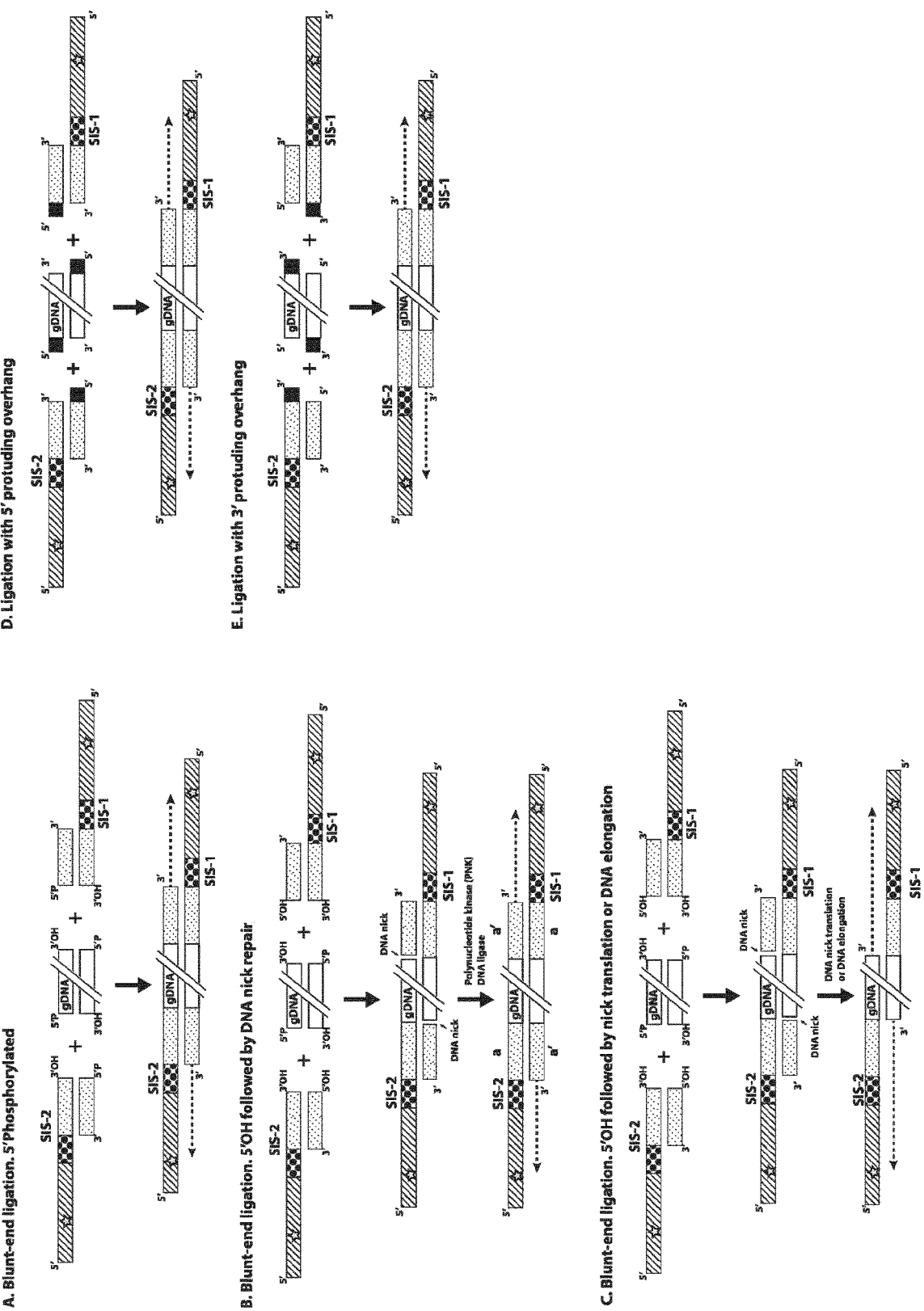

Figure 4
Homology and complementarity betwen oligos
Adaptor containing strand identifier sequence (SIS)
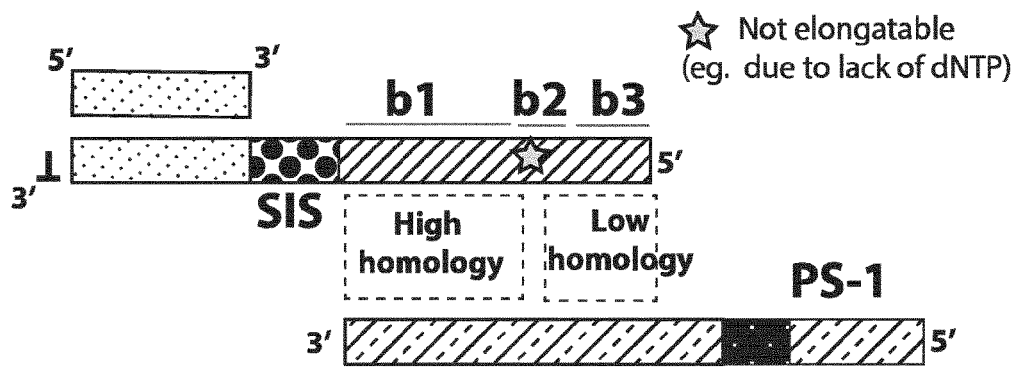
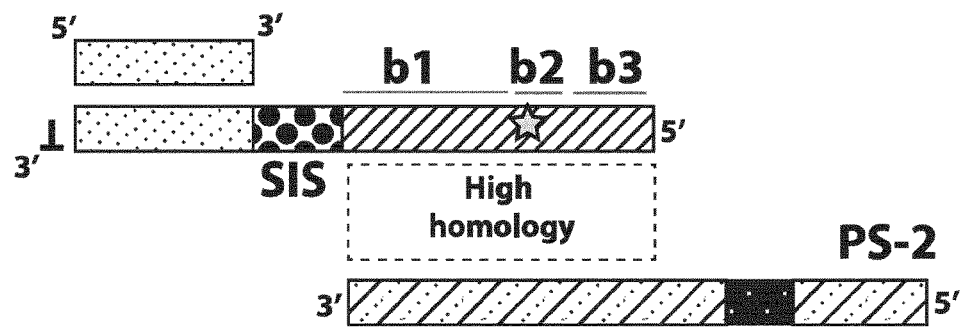
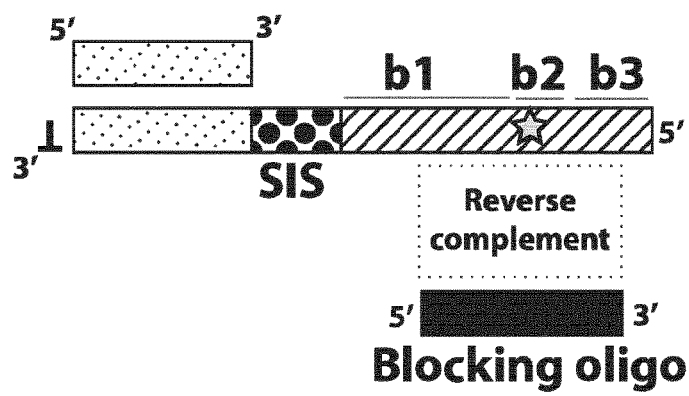

Figure 5
1. Adaptor annealing
2. Partial elongation
3. Pre-elongated strand indexed adaptor
4. Ligation of pre-elongated adaptors
5. Proceed with asymetric amplification
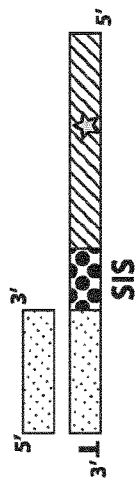
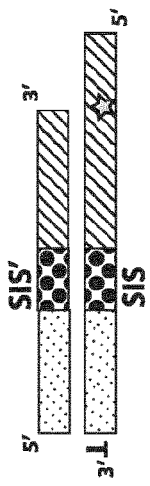
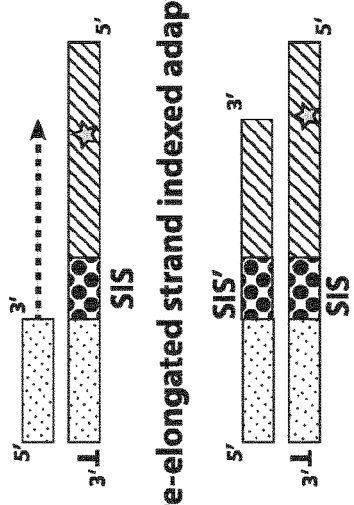
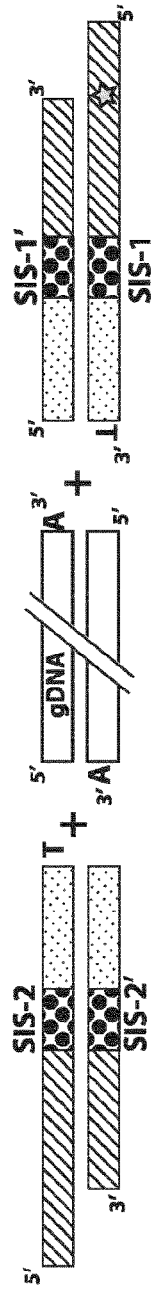
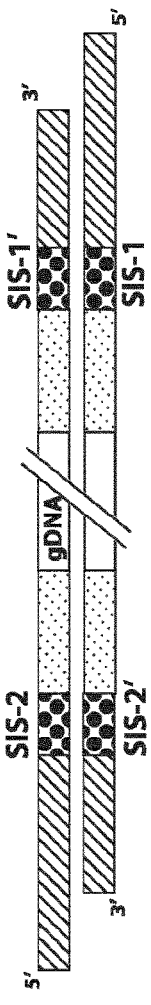

Figure 6

1. Use of pre-elongated adaptors

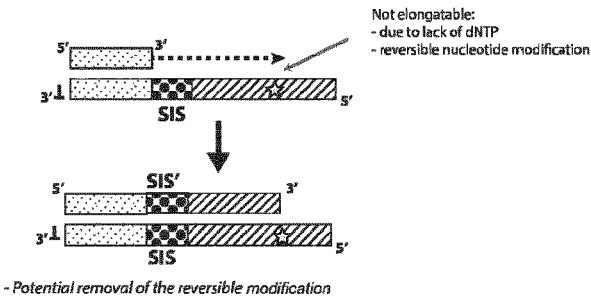

- Potential removal of the reversible modification

1.2 Ligation of the adapter

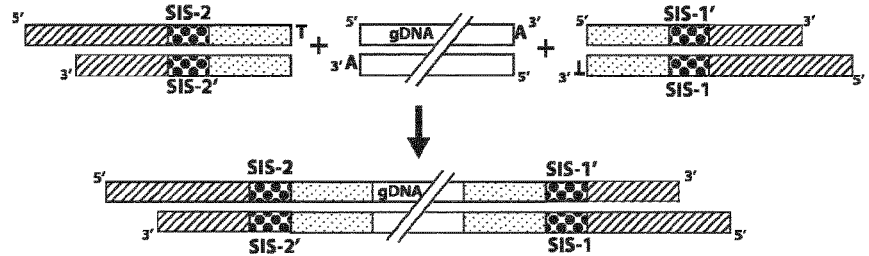

2. Add reaction mix 1
- PCR enzyme buffer with all dNTPs (Optional: use a hot-start DNA polymerase, only active after denaturing DNA)
- Mix contains PS-1 oligo and blocking oligo. The PS-1 comprising the first index sequence. Denature DNA.
- Incubate 60 seconds at 48 °C to prime reaction.
- Incubate 60 seconds at 72 °C to displace blocking oligo and finish elongation from PS-1.

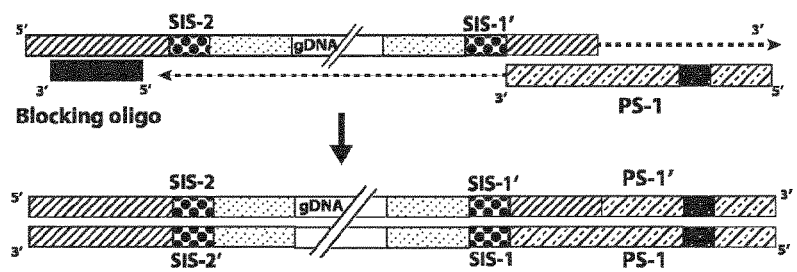

3. Add reaction mix 2
- Mix 2 contains oligo PS-2

3.1 Denaturation and annealing to elongate PS-2 and PS-1
     - Denature and anneal at 60°C to elongate PS-2. Only the strand binding PS-2 is shown.
     The other strand will be incorporated in the second cycle of the PCR

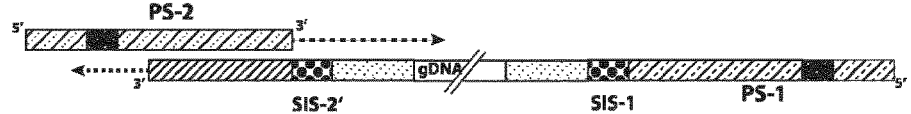

3.2 Proceed with regular PCR reaction. Please note asymmetry.

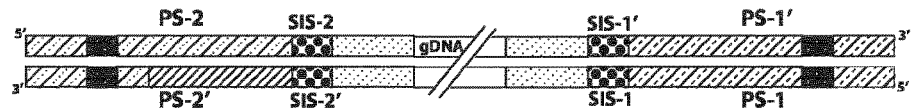

4. Proceed to target enrichment and/or sequencing

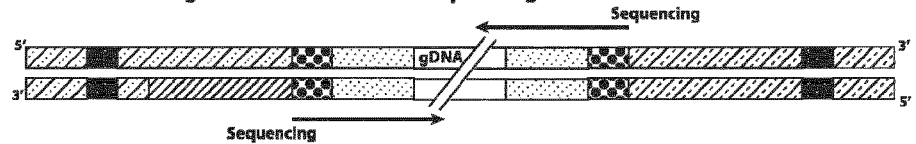

Figure 8
1. Use IVT to amplify one of the strands
- PS-1 contains a promoter for in vitro transcription in the 5' region (eg. T7, T3, SP6...)
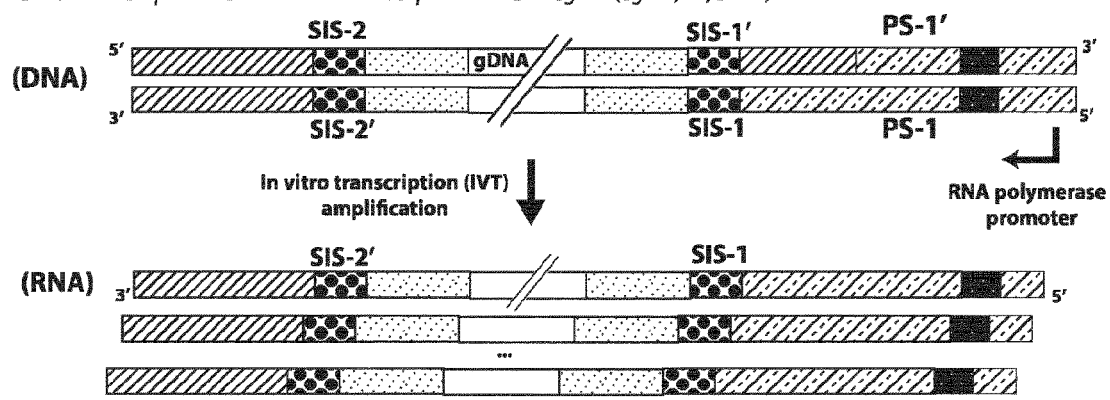
2. Generate second strand by reverse transcription
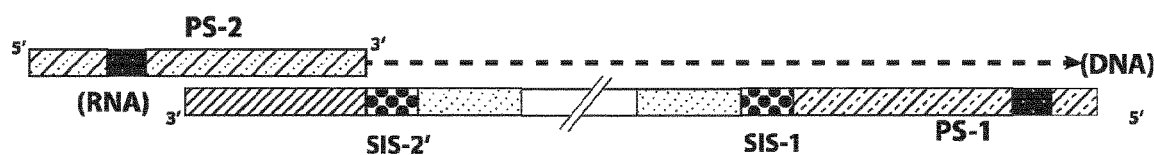
3. Amplify the cDNA by PCR
- Use as primers IS-1b and IS-2.
- Optionaly IS-1b can be diferent from IS-1 (eg., not containing the RNA polymerase promoter)
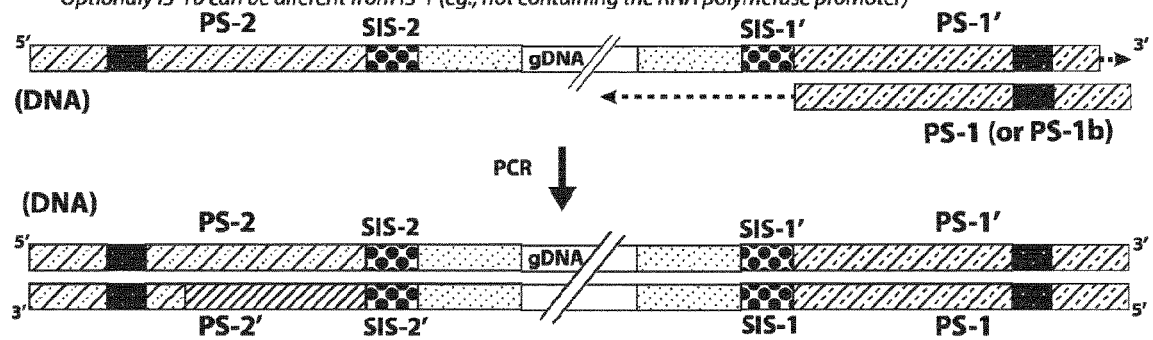

METHODS FOR ASYMMETRIC DNA LIBRARY GENERATION AND OPTIONALLY INTEGRATED DUPLEX SEQUENCING

BACKGROUND OF THE INVENTION

Fields, such as cancer therapeutics, forensics, paleo-genomics, evolution and toxicology, require high-accuracy sequencing and detection of low incidence mutations. Such mutations might even be present in less than 1% of the cells, such as with cancer. This low incidence-genetic diversity is difficult to assess with conventional next generation sequencing due to a high background error rate not only in the sequencing itself, but in the amplification of the genomic DNA prior to sequencing. Deoxyribonucleic acid (DNA) polymerases can introduce misinsertions at a frequency of $10^{-4}$ to $10^{-6}$. When these misinsertions occur early in the generation of the DNA library, such as during first strand synthesis, they can become indistinguishable from low-frequency mutations.

For example, single-cell sequencing, single-stranded molecular barcoding, and circle sequencing (CircSeq) may involve sequencing DNA derived from a single strand of DNA. During the first round of amplification, DNA polymerase may propagate errors to the daughter molecules. In single-cell sequencing, random primers may be used with a DNA polymerase with helicase activity to displace one of the two strands. But the combination of random primers and strand displacement can result in random priming of the newly copied strand and thus, the generation of copies of copies. In the process, any initial misincorporation error will be passed to the copies of copies. As all the genetic information was derived from a single cell, it is impossible to tell whether the sequencing reads represent an error from the original single-strand synthesis or a genetic variant.

CircSeq and single-stranded barcoding may also introduce misinsertions during first round synthesis, an error which may then be propagated to daughter molecules and erroneously scored as a mutation. The same misinsertion error post-isolation is unlikely to occur in the same DNA sequence from other cells or sub-clonal populations. The original error therefore, could not necessarily be identified, accounted for, and/or corrected via post-hoc analysis, instead resulting in errors that may appear to be a sub-clonal mutations.

Duplex sequencing differs from methods relying solely on fidelity of first-strand synthesis, such as the methods described above. Prior to first strand synthesis, duplex sequencing introduces randomized duplex tags onto both ends of the original double-stranded DNA fragment in a complementary fashion. These molecular identifier sequences may be encoded into adaptors that are ligated to each end of a double-stranded DNA so that each end of the double-stranded DNA receives a different molecular identifier sequence. If an error is introduced by DNA polymerase into one of the two strands of DNA during first strand-synthesis or any subsequent synthesis/amplification step, the other strand provides a basis of comparison by, for example, reference to a set of single-stranded consensus sequences. Once all the single strand consensus sequences are read during sequencing, the molecular identifier sequence on each end of each strand of the original DNA fragment can be matched during alignment.

To detect post-isolation errors which occur during synthesis steps subsequent to the first-synthesis step, each strand can be aligned with its same-strand sisters during alignment of the single-strand consensus sequences using the molecular identifier sequence. Any differences in the read sequence can be attributed to misinsertions during a synthesis step subsequent to the first synthesis step.

To detect post-isolation errors which occur during the first synthesis step, each strand can be aligned with its opposite-strand partner during alignment of the duplex consensus sequences (again, using the molecular identifier sequences). Any differences in the read sequences observed by such a comparison may be attributed to misinsertions during the first synthesis step.

If a particular difference is found in both partner strands of the DNA with the same molecular identifier sequence at both ends of the DNA, then the particular difference may be attributed to a mutation or polymorphism existing in the DNA as extracted from the cell. Low incidence mutations in a subset of cells can be identified during the alignment of the total sequence readout by identifying strands with substantially similar sequences but having different molecular identifier sequences.

Conventionally, duplex sequencing methods have relied on "Y-adaptors" (also known as forked adaptors) to impart asymmetry. Y-adaptors have non-complementary sequences at the ends opposite the end which is ligated, thus imparting different sequences onto the 5' and 3' ends of the DNA being ligated. Y-adaptors used for duplex sequencing, however, may require structural modifications and/or the addition of inefficient steps to the process. For example, Y-adaptors may require a pre-elongation step followed by closure of a nick in the body of the Y. Y-adaptors may also require annealing of additional sequences, e.g., to generate double-stranded unique molecular identifier sequences. Use of Y-adaptors may also result in the generation of non-specific products, such as primer dimers.

Other known approaches involve the use of adaptors with hairpins to generate asymmetry. In such approaches, asymmetry is achieved by nesting particular nucleotide sequences into a hairpin structure having a loop, and then cleaving the apex of the loop after ligation. However, the functionality of such approaches may be limited.

There remains a need for improved methods of generating a DNA library which can be coupled to integrated sequencing error identification/correction, e.g., by tracking both strands of a duplex DNA sample (such as genomic DNA fragments) to detect very low frequency mutations and polymorphisms. There further remains a need for such methods which do not require specific pre-configured adaptor molecules (such as Y-adaptors) and/or costly or time-consuming modifications, such as pre-elongation and nick closing, to conventional nucleic acid adaptors used to construct the DNA library. For example, there remains a need for efficient and reliable methods of detection of rare or low-frequency mutations and polymorphisms in cancer cells, chimeric cells, and other forms of intra-subject genetic polymorphisms. There also remains a need for improved methods of generating a DNA library which methods may track both strands of the same DNA molecule and be performed in one pot and/or without wash steps. There also remains a need for improved methods of producing asymmetric fragmented DNA libraries having different molecular identifier sequences on each end of a DNA fragment to be sequenced or analyzed.

SUMMARY OF THE INVENTION

Herein provided is a method for generating one or more DNA products comprising a first and second index sequence (IS), the first and second ISs having different nucleotide sequences and allowing for identification of the source of a PCR sample, said method comprising:

(I) ligating, in a reaction mixture, a first adaptor comprising a first strand identifier sequence (SIS) to one end of a double-stranded DNA having two ends, and a second adaptor comprising a second SIS to the other end of the double-stranded DNA, the first and second SISs having different nucleotide sequences, to obtain an adapted double-stranded DNA comprising a single-stranded 5' overhang at each end;

(II) denaturing the adapted double-stranded DNA to obtain at least one single-stranded DNA template;

(III) decreasing the temperature under conditions that promote: (A) annealing of (i) a blocking oligonucleotide and (ii) a first primering sequence (PS) comprising a first index sequence (IS) to the at least one single-stranded template, the blocking oligonucleotide having an annealing temperature to the single-stranded template equal to or higher than the annealing temperature of the first PS;

(IV) without changing the temperature, adding to the reaction mixture a second PS comprising a second IS;

(V) incubating at a temperature that allows the blocking oligonucleotide to detach from the at least one single-stranded template and elongation from the first PS to proceed;

(VI) denaturing to obtain at least one single-stranded DNA comprising the first IS; and (VII) incubating under conditions that promote annealing of the second PS to the at least one single-stranded DNA comprising the first IS and subsequent DNA polymerization to obtain one or more DNA products comprising a first and second IS, the first and second ISs having different nucleotide sequences.

In an embodiment, the ligating in (I) proceeds at a temperature of 12-25° C.

In an embodiment, the denaturing in (II) proceeds at a temperature of 85-105° C.

In an embodiment, the temperature at which the blocking oligonucleotide anneals to the single-stranded template in (III) is in the range of 44-52° C.

In an embodiment, the temperature that allows the blocking oligonucleotide to detach from the single-stranded template and elongation from the second PS to proceed in (V) is in the range of 60-75° C.

In an embodiment, the denaturing in (VI) proceeds at a temperature of 85-105° C.

In an embodiment, the conditions that promote annealing of the second PS to the at least one single-stranded DNA comprising the first IS and subsequent DNA polymerization in (VII) comprise incubating at a temperature higher than the annealing temperature at which the blocking oligonucleotide anneals to the at least one single-stranded template.

In an embodiment, the temperature higher than the annealing temperature at which the blocking oligonucleotide anneals to the at least one single-stranded template is in the range of 57-65° C. In an embodiment, the method further comprises performing (I)-(III) in a reaction mixture lacking at least one of dATP, dTTP, dCTG, or dGTP, with the proviso that when dTTP is lacking dUTP is also lacking.

In an embodiment, the method further comprises adding to the reaction mixture in (IV) the dNTP or dNTPs lacking in (I)-(III).

In an embodiment, the method comprises partially elongating the adapted double-stranded DNA in the presence of a dNTP mixture lacking at least one of dATP, dTTP, dCTG, or dGTP, with the proviso that when dTTP is lacking dUTP is also lacking.

In an embodiment, the partial elongation occurs either prior to or immediately after the ligating in (I). Herein is also provided a method for generating an asymmetric genomic DNA library without the use of a forked adaptor, the method comprising:

(I) ligating, in a reaction mixture, a first adaptor comprising a first strand identifier sequence (SIS) to one end of a double-stranded genomic DNA fragment, and a second adaptor comprising a second SIS to the other end of the double-stranded DNA, the first and second SISs having different nucleotide sequences, to obtain an adapted double-stranded DNA comprising a single-stranded 5' overhang at each end;

(II) optionally partially elongating the adapted double-stranded DNA in the presence of a dNTP mixture lacking at least one of dATP, dTTP, dCTG, or dGTP, with the proviso that when dTTP is lacking dUTP is also lacking;

(III) denaturing the adapted double-stranded DNA to obtain at least one single-stranded DNA template;

(IV) annealing a first primering sequence (PS) comprising a first index sequence (IS) to the at least one single-stranded template;

(V) incubating under conditions that allow for DNA polymerization from the first PS and/or the at least one single-stranded template;

(VI) denaturing to obtain at least one single-stranded DNA comprising the first IS;

(VII) annealing a second PS to the at least one single-stranded DNA comprising the first IS under conditions that allow for DNA polymerization; and (VIII) obtaining an asymmetric genomic DNA library of amplified DNAs comprising a first and second IS, the first and second ISs having different nucleotide sequences.

BRIEF DESCRIPTION OF THE DRAWINGS

FIG. 1: Schematic representation of an adaptor, a first primering sequence, a second primering sequence, and a blocking oligo for use in DNA library generation. An adaptor containing an SIS is shown as a partially double-stranded molecule of DNA with a single nucleotide (T) 3' overhang. The adaptor could be formed by the annealing of two DNA or two RNA oligonucleotides (short and long), or by the annealing of an RNA and DNA oligonucleotide, one being shorter than the other. The adaptor as shown has a double stranded segment at one end (Region A) (which may be blunt ended or may be substituted by a 3' or 5' overhang (as shown contains a single-nucleotide T 3' overhang) to facilitate ligation to target double stranded DNA molecules (e.g., genomic DNA or "gDNA"). At the other end the adaptor may have a single-stranded 5' overhang comprising a SIS and a primering sequence-binding region (Region B), which in turn may comprise separate sub-sequences: a first primering sequence-binding sequence (b1) and/or a second-primering sequence-binding sequence-(b3) as well as a nucleotide (star) or nucleotide sequence (b2) at which elongation is stopped (e.g., due to an omitted dNTP in the elongation mix). The first primering sequence (PS-1) as shown is a single-stranded oligonucleotide containing a first index sequence (IS-1; black with white dots) and the second primering sequence (PS-2) as shown is a single-stranded oligonucleotide containing a second index sequence (IS-2;

Figure 7:
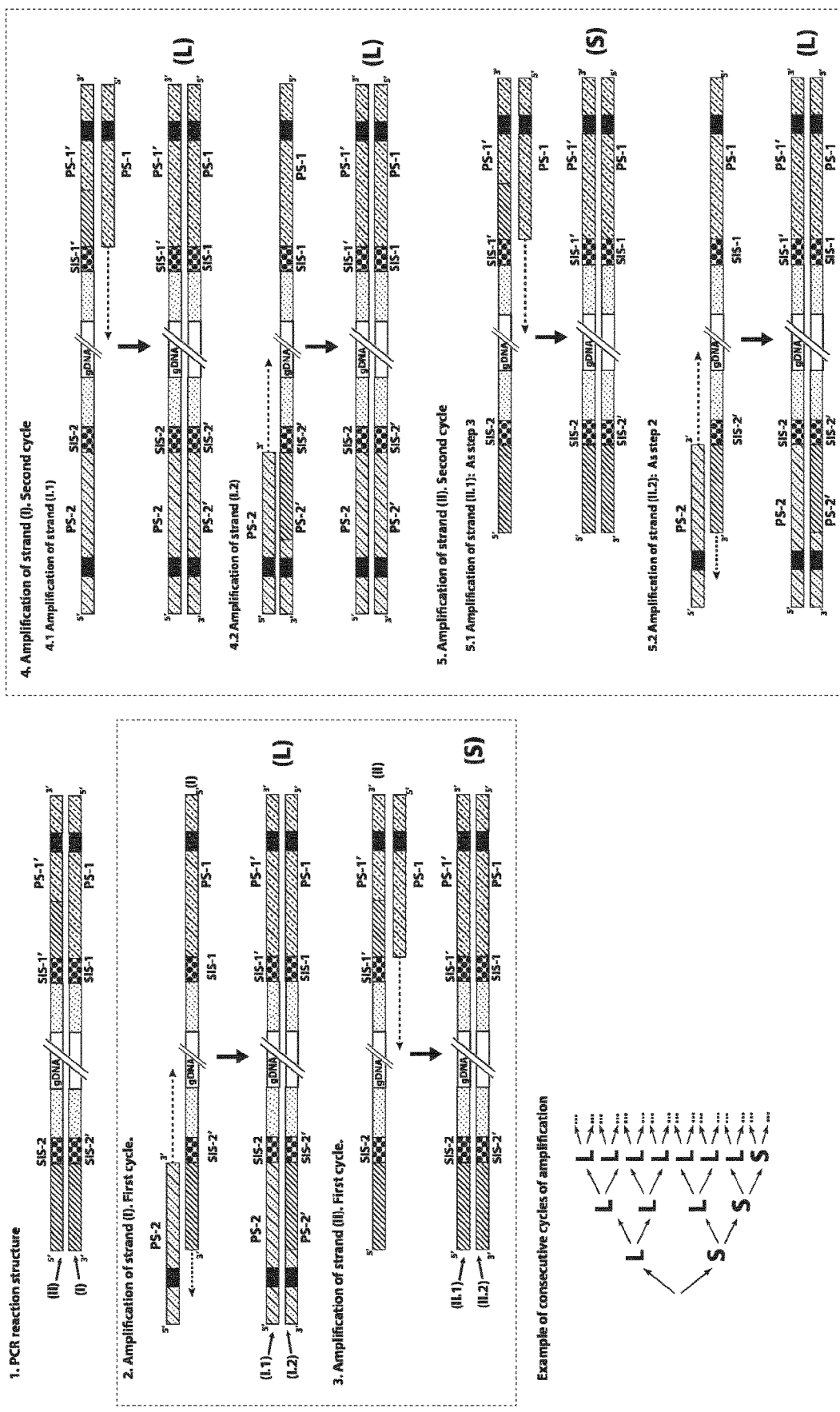

black with white dots). The blocking oligo may be a single-stranded DNA or RNA, and may further comprise locked nucleic acids (LNAs) at least within the 3'end.

FIG. 2: Outline of an implementation of the method using an incomplete mix of dNTPs after ligation of the adaptors to the target molecule. Sequences indicated with a prime (') symbol correspond to a reverse complementary sequence. For example, SIS-1' is the reverse complement to SIS-1.

FIG. 3: Adaptor containing the SIS can be ligated in multiple ways. (A) Blunt end ligation with 5'phosphate and 3'OH. (B) Blunt end ligation with 5'OH and 3'OH will produce a double-stranded DNA molecule with 5' overhangs and DNA nicks. DNA nicks can be closed by phosphorylation of the 5'OH (e.g., by using polynucleotide kinase (PNK)) and DNA ligation. (C) Blunt end ligation with 5'OH and 3'OH will produce a double-stranded DNA molecule with 5' overhangs and DNA nicks. DNA nicks can be removed by the use of a DNA polymerase with strand displacement activity (e.g., nick translation), or by performing DNA elongation at a temperature that will destabilize the binding between a and a' in the adaptors containing the SIS. In both cases DNA elongation will stop at b2 (marked as a star). (D) Ligation of adaptor with protruding 5' overhang. (E) Ligation of adaptor with protruding 3' overhang.

FIG. 4: Homology and reverse complementarity between the various oligonucleotides. This figure shows possible areas of homology between a first primering sequence and an adaptor, between a second primering sequence and an adaptor, as well as between a blocking oligo and an adaptor. The first primering sequence-binding sequence, b1, may have high homology to the first primering sequence, PS-1, or a portion thereof, but the second primering sequence-binding sequence, b3, may have low homology to the first primering sequence (or a portion thereof). In contrast, the second primering sequence, PS-2, may have high homology to both the first and second primering sequence-binding sequences, b1 and b3 respectively, in addition to b2. The blocking oligonucleotide may be the reverse complement to sequences within b3, b2, and b1, and might optionally not anneal to the entirety of b1 or b3 or might not anneal to b2 at all.

FIG. 5: Adaptor preparation options. Adaptors may be elongated prior to ligation with the target molecule as shown in (1) and (2) or ready-made as shown in (3) to avoid an elongation step prior to ligation and amplification as shown in (4) and (5).

FIG. 6: Outline of an implementation of the method using a complete mix of dNTPs after ligation of the adaptors to the target molecule. In one implementation, adaptors can be pre-elongated (1). This can be performed using a mix depleted for one specific dNTP or by the presence of a DNA modification that prevents DNA elongation. Adaptors may then be purified and ligated with a target molecule or preferably with multiple target molecules such as gDNA fragments as shown (1.2). DNA modification (star) can be removed before, during or after the ligation step. 2) The ligated sample may then be denatured in the presence of a first primering sequence comprising a first index sequence (IS-1; black with white dots), a blocking oligonucleotide, and a PCR mix with all the dNTPs. To prevent the filling of the 5'protuding overhangs, DNA elongation is not allowed to proceed before the denaturing step and binding of PS-1 and blocking oligo. This can be achieved by using a hot start DNA polymerase (that is not active before the denaturing step), or by adding the DNA polymerase (or any other critical element for the PCR like dNTPs) only after the denaturation and annealing step. 3) A second primering sequence comprising a second index sequence (IS-2; black with white dots) is added to the reaction mix and PCR proceeds as in FIG. 2.

FIG. 7: Intermediate steps of PCR amplification. FIG. 7 shows the first two cycles of amplification of the PCR depicted in FIG. 2 step 3. Depending on the specific strand used as template, the amplification will produce either a short double-stranded DNA(S) or a long double-stranded DNA containing the full sequence of the first and second primering sequence (L). Due to the exponential amplification proprieties of PCR, the(S) fragment will be over competed by the amplification of (L) fragments.

FIG. 8: It is possible to use an intermediate step based on RNA. 1) After step 2 in FIG. 2, double-stranded DNA may be amplified by in vitro transcription (IVT) (1). This resulting RNA may be reverse transcribed using a primering sequence (PS-2) comprising a first index sequence (IS-1; black with white dots) as shown in (2). Produced cDNA may then be amplified with another primering sequence (PS-1 or PS-1b) and PS-2. Note that the primering sequence may exclude one or more sequences required for the IVT amplification.

Figure 9:
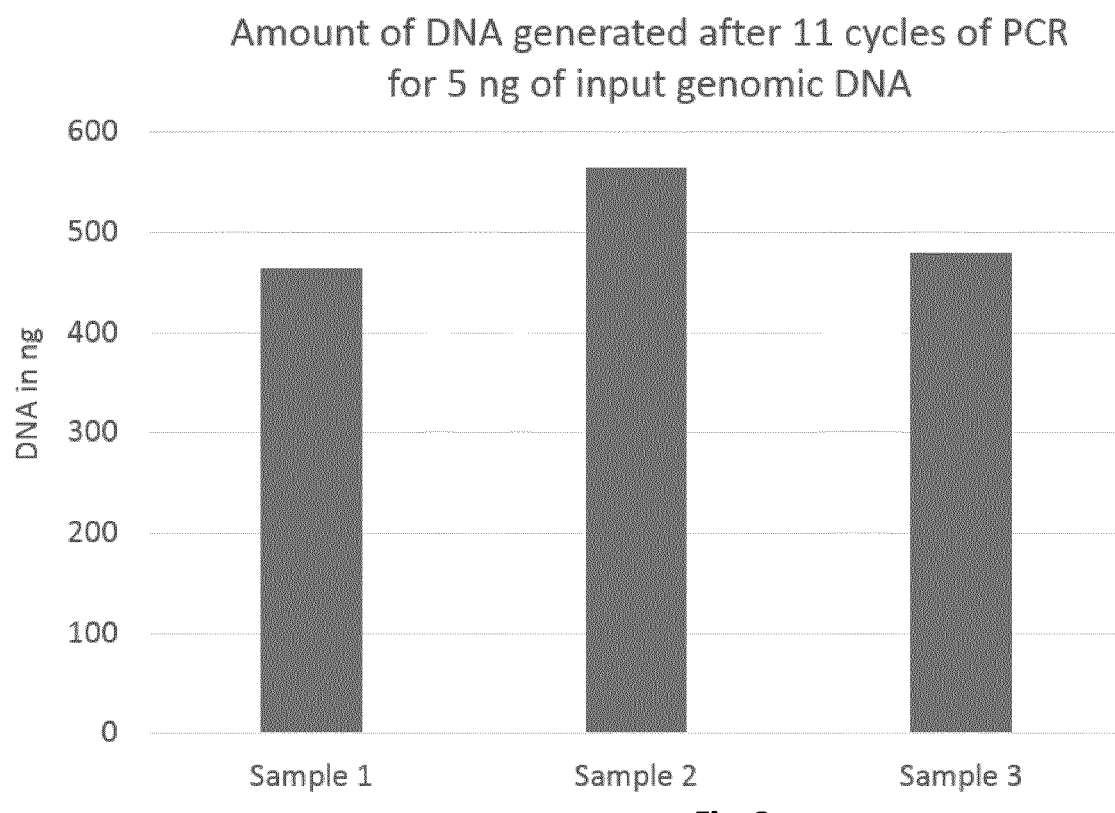

FIG. 9. The workflow for the protocol which allows to prepare libraries with duplex strand identifier sequences (SIS) on both ends of the molecule. This protocol includes target capture and is what we used to prepare the libraries shown in the other figures.

Figure 10:
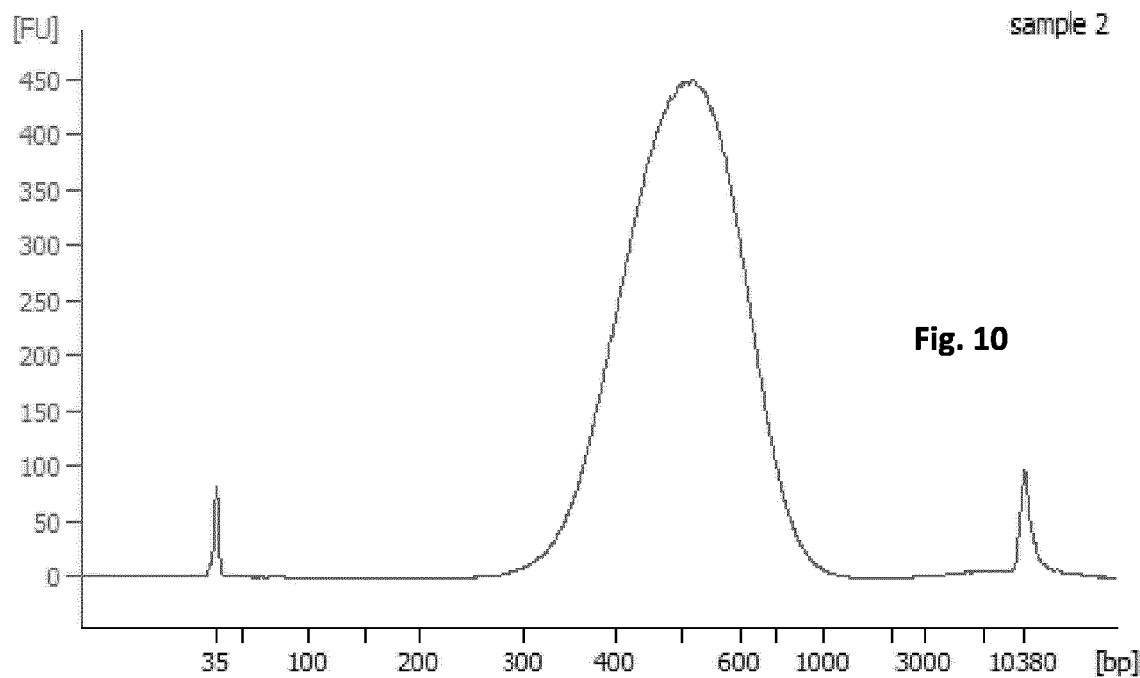

FIG. 10. Typical DNA yields after pre-capture PCR for an input amount of 5 ng genomic DNA.

Figure 11:
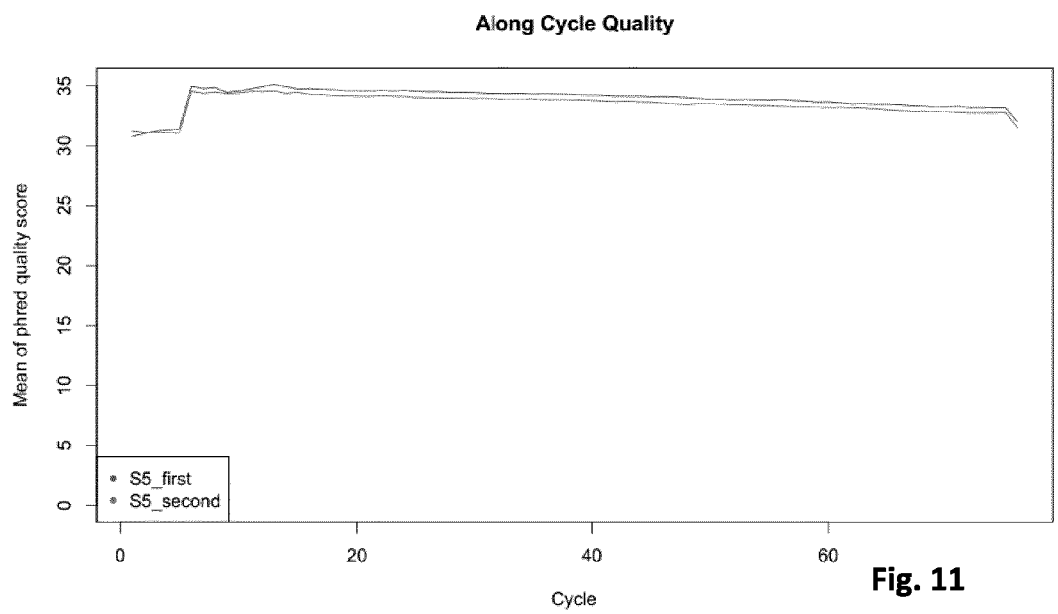

FIG. 11. A Bioanalyzer trace for a typical sample after the pre-capture PCR, showing the size distribution.

Figure 12:
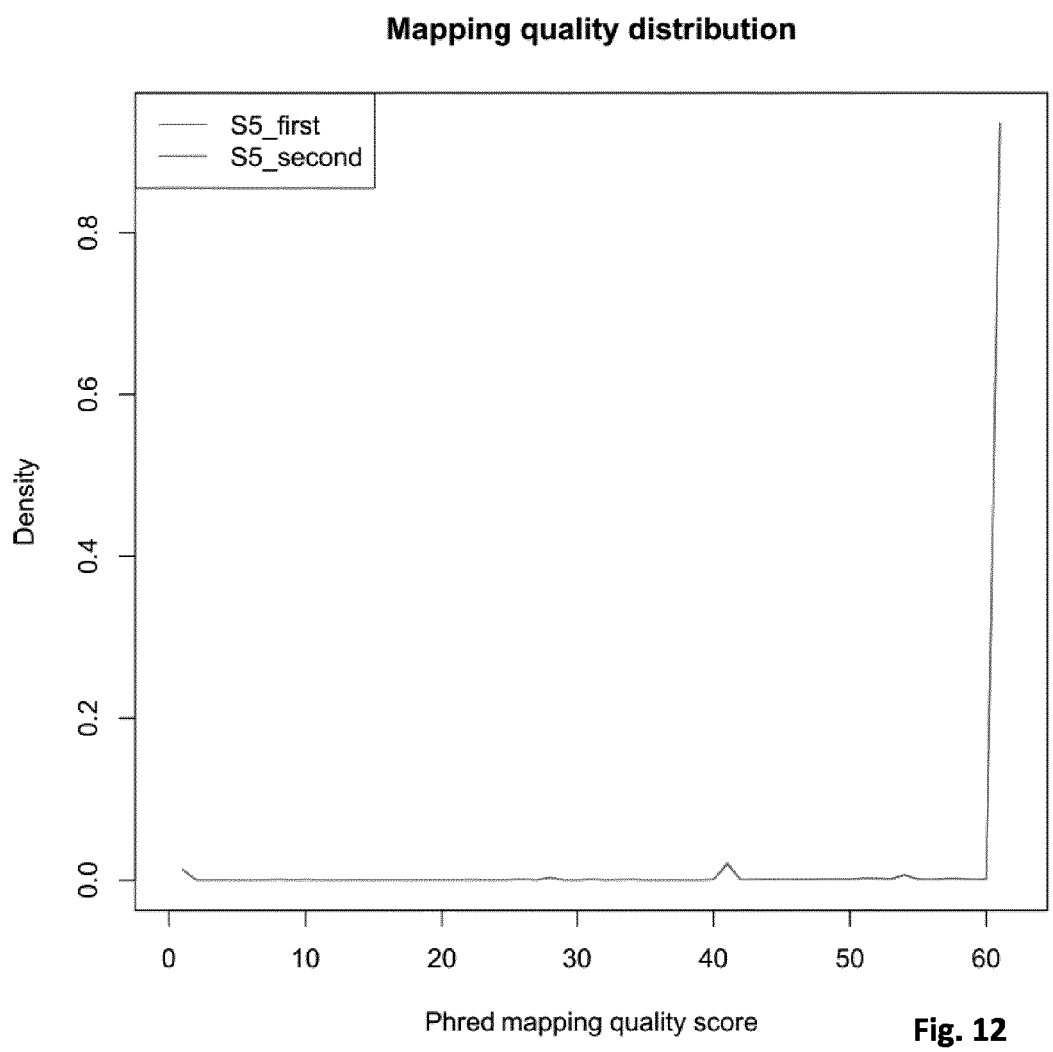

FIG. 12. Sequencing quality for a typical sample.

Figure 13:
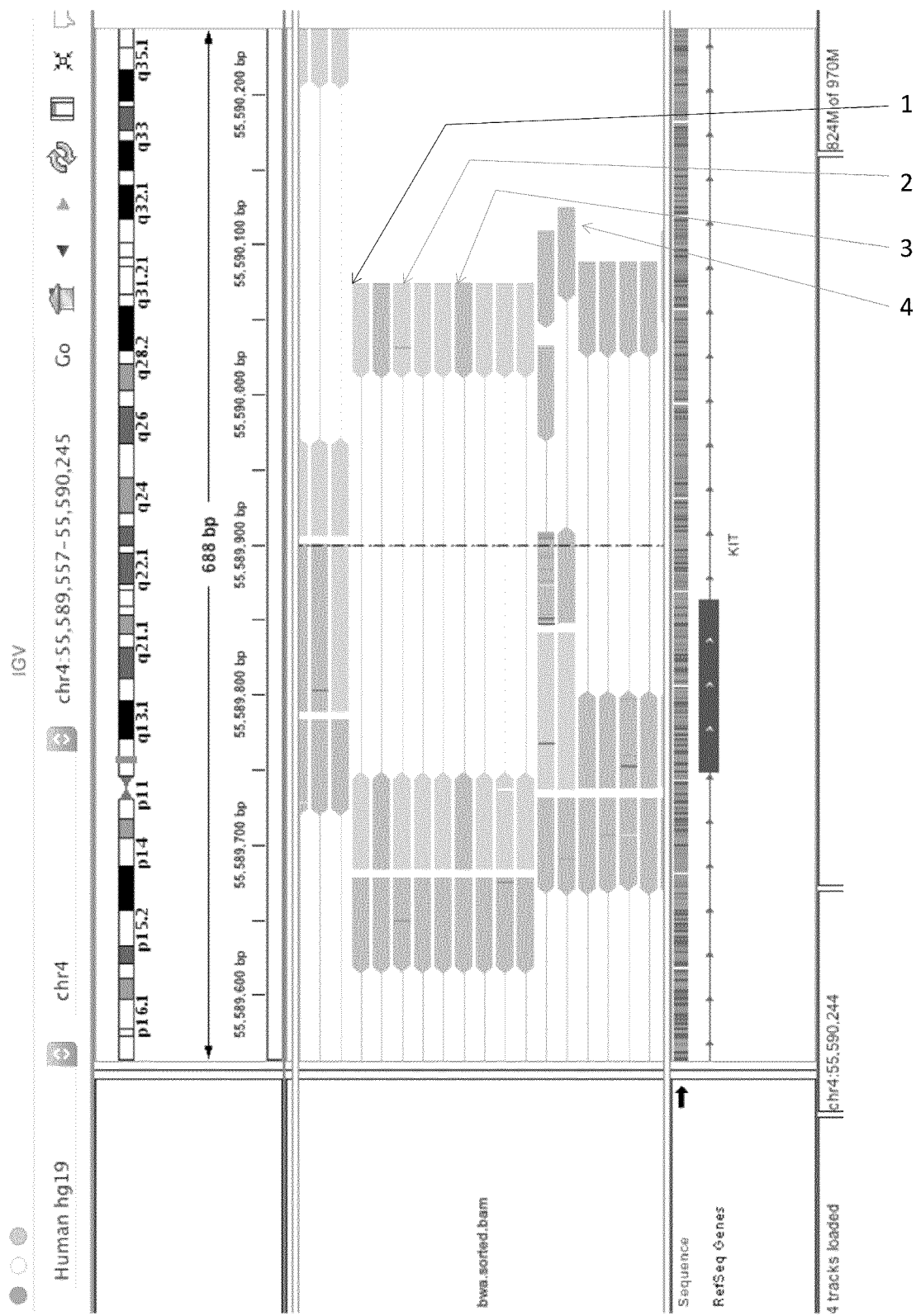

FIG. 13. Mapping quality distribution for a typical sample.

DETAILED DESCRIPTION OF THE INVENTION

The particulars shown herein are by way of example and for purposes of illustrative discussion of the various embodiments only and are presented in the cause of providing what is believed to be the most useful and readily understood description of the principles and conceptual aspects of the methods and compositions described herein. In this regard, no attempt is made to show more detail than is necessary for a fundamental understanding, the description making apparent to those skilled in the art how the several forms may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope to those skilled in the art.

Unless otherwise defined, all technical and scientific terms used herein have the same meaning as commonly understood by one of ordinary skill in the art to which this invention belongs. The terminology used in the description herein is for describing particular embodiments only and is not intended to be limiting. As used in the description and the appended claims, the singular forms "a," "an," and "the" are intended to include the plural forms as well, unless the context clearly indicates otherwise.

Unless indicated to the contrary, the numerical parameters set forth in the following specification and attached claims are approximations that may vary depending upon the desired properties sought to be obtained and thus may be modified by the term "about". At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Definitions

A "strand identifier sequence" or "SIS" refers to a nucleotide sequence of 4 to 30 nucleotides in length that functions as a distinct molecular tag for a nucleic acid strand prior to PCR amplification and allows for (1) identification of the nucleic acid strand from which a PCR amplification product is derived, (2) consensus-based error correction, including single-strand consensus sequence and duplex consensus sequence error correction, and/or (3) molecular counting.

An "index sequence" or "IS" refers to a sequence of nucleotides that functions to identify the source of a PCR-amplified sample. A single IS may be used to identify the source of a PCR-amplified sample or an IS may be used in combination with one or more other ISs to identify the source of a PCR-amplified sample.

A "primering sequence" or "PS" refers to a nucleotide sequence of at least 20 nucleotides in length comprising an index sequence and a region of complementarity to a target nucleic acid a part or all of which is to be elongated or amplified.

Fragmentation

In some embodiments, methods as described herein will involve the use of genomic and mitochondrial DNA to be sequenced and determination of such information as the location and coding of genes, promoters, exons, introns, and potentially epigenetic information, such as CpG islands, and methylation, potentially in conjunction with bisulfide conversion. Genomic DNA may be chromosomal DNA or circular DNA. Alternatively, with exosome sequencing, mRNA may be reverse transcribed into complementary DNA or cDNA, and said cDNA may be fragmented, or it may be of a small enough length that it may be sequenced without fragmentation. The complementary cDNA, fragmented or non-fragmented, may be single-stranded, and could then be made double-stranded by annealing random primers and/or other primers and elongating the primers to be complementary to the cDNA, thus forming a double-stranded cDNA. In some embodiments, the double-stranded cDNA and mitochondrial and/or genomic DNA must be fragmented prior to sequencing. Fragmentation may be achieved by several means including but not limited to sonication, ultrasonication, mechanical shearing, partial digestion via for example restriction enzyme digestion, etc. Fragmentation may result in a fragmented genomic or mitochondrial DNA being 50 to 10000 base-pairs in length, preferably 200 base-pairs to 800 base-pairs in length, more preferably 300 to 500 base-pairs in length, and more preferably still 400 base-pairs in length. The DNA fragments, whether from cDNA, genomic DNA, or mitochondrial DNA, may be sized-fractionated, for example by agarose gel electrophoresis; gel chromatography; equilibrium density-gradient centrifugation, including sucrose gradient centrifugation, percol gradient centrifugation, cesium-chloride centrifugation; and other means.

Adaptor Ligation/Insertion

After fragmentation, in the case of genomic DNA or chromosomal DNA or reverse transcription followed by formation of double-stranded DNA, adaptors may be ligated or linked to each of the ends of the fragmented double-stranded DNAs. FIG. 1 shows an embodiment of an adaptor containing an SIS. The adaptor as shown comprises a partially double-stranded molecule of DNA with a single nucleotide (T) 3' overhang at the end being annealed to the double-stranded fragmented DNA, although the adaptor could be formed by the annealing of two DNA or two RNA oligonucleotides (short and long), or by the annealing of an RNA and DNA oligonucleotide, one being shorter than the other. The adaptor as shown has a double stranded segment at one end (Region A) (which may be blunt ended or may be substituted by a 3' or 5' overhang (as shown contains a single-nucleotide T 3' overhang) to facilitate ligation to target double stranded DNA molecules (e.g., genomic DNA or "gDNA"). At the other end the adaptor may have a single-stranded 5' overhang comprising a SIS.

FIG. 2 illustrates in step "1" the ligation of adaptors to the fragmented DNA (labelled for illustrative purposes only as "gDNA" for genomic DNA, however other forms of DNA are contemplated for sequencing). An adaptor may be single-stranded, provided it is ligate-able to each of the 5' ends of the double-stranded DNAs. More preferably, an adaptor comprises a double-stranded sequence at the end being annealed to the double-stranded DNA. In this regard, one of the two strands of the double-stranded sequences of the adaptor will be ligated to the 3' end of the fragmented double-stranded DNA, and the other of the two strands of the double-stranded sequences of the adaptor will be ligated to the 5' end of the fragmented double-stranded DNA.

The ends of the double-stranded sequences of the adaptors being ligated to the fragmented double-stranded DNA are not limited and may comprise blunt ends, 3' overhangs, and 5' overhangs, as shown in FIG. 3. In this regard, the 5'ends of the adaptors being ligated could either terminate with a 5'-phosphate or a 5'-OH. If a 5'-OH is at the adaptor end to be ligated to the target nucleic acid, it may be necessary to use a polynucleotide kinase to complete the backbone and join the 5'-OH of the adaptor to the 3'-OH of the fragmented DNA. Alternatively, once the 3'-OH end of the adaptor has been ligated to the 5' phosphate of the fragmented DNA, the double-stranded portion of the adaptor would still have a nick, and it could be de-annealed or melted. The 3'-OH of the fragmented DNA could then be elongated via the partial elongation, elongation, or full elongation described below. In some embodiments a one nucleotide overhang able to be ligated by T-4 ligase from the T-4 bacteriophage is preferable. Thus, in some embodiments, an adenine may be added to each of the 3' blunt ends of the fragmented DNA prior to adaptor ligation, and the adaptor may have a thymidine overhang on the 3' end to base-pair with the adenine added to the 3' end of the fragmented DNA. In some embodiments, an adenine may be added to each of the 3' blunt ends of the fragmented DNA prior to adaptor ligation, and the adaptor may have a phosphorothioate bond before the terminal thymidine on the 3' end to base-pair with the adenine added to the 3' end of the fragmented DNA. The phosphorothioate bond before the terminal thymidine will prevent an exonuclease from trimming the thymidine, thus creating a blunt end when the end of the adaptor being ligated is double-stranded.

In some embodiments, the adaptors may be linked to the fragmented DNA using processes such as transposase-based fragmentation as described in WO 2010/048605, herein incorporated by reference, or integrase-based fragmentation, as described in WO 2015/106890A1, also herein incorporated by reference. In such embodiments, specific DNA oligonucleotides, such as the adaptor sequences may be inserted into the genome prior to, or during fragmentation, or alternatively ligated using the transposase or integrase enzymes immediately after fragmentation.

The Strand Identifier Sequences of the Adaptors

The adaptors may also comprise a strand identifier sequence ("SIS") at least within the sequence of the adaptor being ligated to the 5' end of the fragmented double-stranded DNA, as show in FIG. 1.

In an embodiment the SIS may be long enough to provide enough permutations to identify each fragmented DNA strand individually or in combination with the other strand identifier sequences. By way of further example, if genomic DNA from 10 different cells is obtained, each cell's DNA being fragmented into 1000 pieces, then there should be a sufficient number of nucleotides in the strand identifier sequences to identify 10,000 DNA fragments (10 cells multiplied by 1000 DNA fragments per cell). Theoretically, therefore it would take a sequence of six nucleotides (assuming four nucleotides: A, T, G, C) to be able to individually identify at least 10,000 fragments of DNA ($4^5$=4096, $4^6$=16,384).

Alternatively, in an embodiment, the SIS may be used in conjunction with the nucleotide sequence of the fragmented DNA during consensus alignment of the fragmented DNA sequences. For example, the ends of the fragmented DNA may be used to identify or assist in identifying each daughter strand of fragmented DNA that was amplified from the original strand of fragmented DNA as isolated from the sample. Alternatively or in addition, the SIS may be used in conjunction with the sequence reads of the ends of the fragmented DNA to identify the daughter strands of fragmented DNA that was amplified from the original strand of fragmented DNA as isolated from the sample. In this regard, when the ends of the fragmented DNA are used in conjunction with the SIS to identify each daughter strand, the number of nucleotides in the SIS may be further reduced. For example, if four nucleotides were read from the ends of the fragmented DNA and were used in conjunction with the SIS, and if 100,000 fragments of DNA required specific identification post-sequencing, then the SIS might only be five nucleotides in length ($4^4$=256 combinations identified by the reads from the end of the fragment, and $4^5$=1024 combinations identified by the SISs, and in combination 256×1024=262,144 strands of fragmented DNA may be identified by the combination of the end reads of the fragmented DNA and SIS.) In an embodiment, 1-100 consecutive nucleotides from one or both ends of the sequence reads of the fragmented DNA may assist in the identification. In an embodiment 2-99, 3-98, 4-97, or 5-96 consecutive nucleotides from one or both ends of the sequence reads of the fragmented DNA may assist in the identification. In alternative embodiments, 6, 7, 8, 10, 15, 20, 25, 30, 40, 50, 60, 70, 80, or 90 nucleotides from the sequence reads of the fragmented DNA may be used to assist in the identification.

FIG. 1 illustrates one possible location for a strand-identifier sequence (labelled as "SIS") on an adaptor. Preferably, the SISs are random or near random sequences of nucleotides. By random, it is meant that it is possible in the synthesis of a SIS, each nucleotide is chosen independently of the previous nucleotide in the sequence. For example, each of the four nucleotides (deoxyribo-adenine monophosphate, deoxyribo-cytosine monophosphate, deoxyribo-guanine monophosphate, and deoxyribo-thymidine monophosphate) would be as likely as the next to be chosen (25% probability) after the selection of the nucleotide prior in the sequence. By near random, it is understood that the conditions determining the next nucleotide in the sequence, including the enzymes determining the next nucleotide in the sequence, may not be fully independent but instead close to independent. For example, one nucleotide, a thymidine, might have a slightly higher probability of being selected, a 25.5% chance, when the previous nucleotide selected in the sequence is also a thymidine. By near random it is understood that for example, after random selection of three adenines in a row, the nucleotide mix might be depleted of adenines, making the selection of thymidine, guanine, or cytosine more likely than adenine. Likewise, in some embodiments, it is preferred that the SIS omit at least one nucleotide (e.g., deoxyribo-adenine monophosphate) or in other words that the SIS consist of only three types of nucleotides. In this context, the conditions determining the next nucleotide in the sequence independently of the previous nucleotide, if random, would mean that there is a 33.33% chance that a particular nucleotide will be selected (i.e. if deoxyribo-adenine monophosphate is omitted, then selection of deoxyribo-cytosine deoxyribose monophosphate, deoxyribo-guanine monophosphate, or deoxyribo-thymidine monophosphate are equally probable).

By being random or near random, it is contemplated that it is extremely unlikely that each of the two adaptors ligated to each of the two 5' ends of the fragmented double-stranded DNA will have the same nucleotide sequences in their SISs. Thus, each fragmented double-stranded DNA can be identified by each of the SISs, possibly by each of the SISs individually, or possibly by the particular combination of each of the SISs. Because an adaptor will be annealed to each of the two 5' ends of the fragmented double-stranded DNA and because it is extremely likely that both adaptors will have SISs with different nucleotide sequences, the two different strand identifier sequences will be known as a first SIS and a second-strand identifier sequence.

In some embodiments, the strand identifier sequences are at least 4 nucleotides in length, in preferred embodiments the strand identifier sequences are at least 7 nucleotides in length, in the most preferred embodiment the strand identifier sequence is 8 nucleotides in length.

In some embodiments, the SISs omit at least one of the four nucleotides, with the proviso that if deoxyribo-thymidine monophosphate is omitted deoxyribo-uracil monophosphate is also omitted. For example, the SIS may omit deoxyribo-adenine monophosphate, deoxyribo-cytosine deoxyribose monophosphate, deoxyribo-guanine monophosphate, or deoxyribo-thymidine monophosphate, with the proviso that if deoxyribo-thymidine monophosphate is omitted then deoxyribo-uracil monophosphate is also omitted from the sequence of the SIS. In this regard, thymidine and uracil are functionally equivalent in encoding genetic information across RNA and DNA and the uracil should not replace thymidine when thymidine is omitted. Alternatively, the strand identifier sequence may omit two or more of deoxyribo-adenine monophosphate, deoxyribo-cytosine deoxyribose monophosphate, deoxyribo-guanine monophosphate, or deoxyribo-thymidine monophosphate, with the proviso that if deoxyribo-thymidine monophosphate is omitted then deoxyribo-uracil monophosphate is also omitted.

However, in the preferred embodiment, only one nucleotide is omitted from the SIS, and thus, the strand identifier sequence will still comprise the other three nucleotides. For example, if deoxyribo-adenine monophosphate is omitted, then it would still comprise deoxyribo-cytosine deoxyribose monophosphate, deoxyribo-guanine monophosphate, and deoxyribo-thymidine monophosphate. For example, if deoxyribo-thymidine monophosphate is omitted, then it would still comprise deoxyribo-cytosine deoxyribose monophosphate, deoxyribo-guanine monophosphate, and deoxyribo-adenine monophosphate, but it would not comprise deoxyribo-thymidine monophosphate. It is preferred that the first SIS omit the same nucleotide as the second SIS and vice versa. For example, if the first-strand identifier sequence omits deoxyribo-adenine monophosphate (adenine), then the second-strand identifier sequence may also omit deoxyribo-adenine monophosphate (adenine). It is further preferred that the all the SISs of all the adaptors omit the same nucleotide. For example, all the SISs of all the adaptors may omit deoxyribo-adenine monophosphate (adenine).

A SIS may form part of a double-stranded duplex after ligation of the adaptor to the fragmented double-stranded DNA by elongating either the 3' end of the fragmented double-stranded DNA or the 3' end of the double-stranded sequence of the adaptor with DNA polymerase—in the process the single-stranded SIS will be a template for DNA polymerase, which will synthesize a new strand of DNA which may be partially or completely complementary to the single-stranded SIS. The reverse complement of a SIS is indicated herein as SIS'. The SIS may be made double-stranded before ligation of the adaptor to the fragmented double-stranded DNA by either elongating the 3' end of the double-stranded sequence of the adaptor or annealing and elongating a random primer such as a random pentamer, hexamer, heptamer, octomer, etc. If the SIS is being made to form part of a double-stranded duplex before or after ligation to the fragmented double-stranded DNA and the SIS lacks one type of nucleotide, the conditions polymerizing the new, preferably complementary strand may omit a nucleotide triphosphate (dNTP) complementary to or which base-pairs with the nucleotide type omitted from the SIS, with the proviso that if dTTP is omitted, dUTP is also omitted. For example if the strand identifier sequence lacks deoxyribo-adenine monophosphate, then the polymerization conditions to synthesize the reverse complement sequence may omit dTTP and dUTP from the reaction mix because once incorporated into the newly synthesized DNA, the deoxyribo-thymidine monophosphate and deoxyribo-uracil monophosphate would normally base-pair with deoxyribo-adenine monophosphate, but for the omission of deoxyribo-adenine monophosphate from the single-stranded SIS.

The Primering Sequence-Binding Region of the Adaptors

In addition to the SIS, the adaptor may also comprise a primering sequence-binding region (e.g., Region B shown in FIG. 1). A primering sequence-binding region, of an adaptor may be: 1) on the same strand of the adaptor being annealed to the 5' end of the fragmented double-stranded DNA, and 2) preferably 5'-downstream of the SIS.

The primering sequence-binding region may comprise separate sub-sequences of high homology (b1) and/or low homology (b3) (b1 and b3 being first and second primering sequence-binding sequences, respectively) to the first primering sequence (PS-1) as shown in FIG. 1 and FIG. 4. A star indicates the site of a nucleotide within a primering sequence-binding region at which elongation may be stopped or paused. The first primering sequence-binding sequence may be 10 to 30 base pairs in length, more preferably 15 to 25 base pairs in length, more preferably still 18 to 23 base pairs in length. In some embodiments, the first primering sequence-binding sequence omits at least one of the four nucleotides, with the proviso that if deoxyribo-thymidine monophosphate is omitted deoxyribo-uracil monophosphate is also omitted. For example, the first primering sequence-binding sequence may omit deoxyribo-adenine monophosphate, deoxyribo-cytosine deoxyribose monophosphate, deoxyribo-guanine monophosphate, or deoxyribo-thymidine monophosphate, with the proviso that if deoxyribo-thymidine monophosphate is omitted then deoxyribo-uracil monophosphate is also omitted from the sequence of the first primering sequence-binding sequence. In this regard, thymidine and uracil are functionally equivalent in encoding genetic information across RNA and DNA and the uracil should not replace thymidine when thymidine is omitted. Alternatively, the first primering sequence-binding sequence may omit two or more of deoxyribo-adenine monophosphate, deoxyribo-cytosine deoxyribose monophosphate, deoxyribo-guanine monophosphate, or deoxyribo-thymidine monophosphate, with the proviso that if deoxyribo-thymidine monophosphate is omitted then deoxyribo-uracil monophosphate is also omitted.

However, in a preferred embodiment, only one nucleotide may be omitted from the first primering sequence-binding sequence, and thus, the first primering sequence-binding sequence will still comprise the other three nucleotides. For example, if deoxyribo-adenine monophosphate is omitted, then it would still comprise deoxyribo-cytosine deoxyribose monophosphate, deoxyribo-guanine monophosphate, and deoxyribo-thymidine monophosphate. For example, if deoxyribo-thymidine monophosphate is omitted, then it would still comprise deoxyribo-cytosine deoxyribose monophosphate, deoxyribo-guanine monophosphate, and deoxyribo-adenine monophosphate, but it would not comprise deoxyribo-thymidine monophosphate.

FIG. 5 shows a pre-elongated adaptor where the reverse complement of the SIS and sequence b1 have been made. If a primering sequence-binding sequence and the SISs are present in a double-stranded duplex prior to the ligation of the adaptors to the fragmented DNA, then the process of elongating the first primering sequence and/or single-stranded template may omit the partial elongation step, as FIG. 6 illustrates. If the reverse complement of a primering sequence-binding sequence is elongated, it is preferable that each sequence of the primering sequence-binding sequence on each strand be fully complementary (100% Watson-Crick base-pairing) to the other sequence on the other strand. For example, FIG. 5 shows several pre-elongated adaptors where the SIS and sequence b1 are present in a double-stranded duplex. If the primering sequence-binding sequence is a single-stranded sequence, the single-stranded sequence may be made double-stranded after ligation of the adaptor to the fragmented double-stranded DNA by elongating either the 3' end of the fragmented double-stranded DNA through the SIS or the 3' end of the double-stranded sequence of the adaptor with DNA polymerase through the SIS in the process the single-stranded first primering sequence-binding sequence will be a template for DNA polymerase, which will synthesize a new strand of DNA which may be complementary to the single-stranded first primering sequence-binding sequence. Alternatively if the first primering sequence-binding sequence is a single-stranded sequence, the single-stranded sequence may be made double-stranded before ligation of the adaptor to the fragmented double-stranded DNA by either elongating the 3' end of the double-stranded sequence of the adaptor through the SIS or annealing and elongating or ligating an annealed complementary sequence to the first primering sequence-binding sequence.

If the single-stranded first primering sequence-binding sequence is being made double-stranded before or after ligation to the fragmented double-stranded DNA and the single-stranded first primering sequence-binding sequence omits one nucleotide, the conditions polymerizing the new, preferably complementary strand to create the double-stranded first primering sequence-binding sequence may omit the nucleotide triphosphate complementary to or which base-pairs with the nucleotide omitted from the single-stranded SIS, with the proviso that if dTTP is omitted, dUTP is also omitted. For example if the single-stranded SIS omits deoxyribo-adenine monophosphate, then the polymerization conditions to synthesize double-stranded first primering sequence-binding sequence may omit dTTP and dUTP because once incorporated into the newly synthesized DNA, the deoxyribo-thymidine monophosphate and deoxyribo-uracil monophosphate would normally base-pair with deoxyribo-adenine monophosphate, but for the omission of deoxyribo-adenine monophosphate from the single-stranded first primering sequence-binding sequence.

In a preferred embodiment, the SIS and the first primering sequence-binding sequence omit the same nucleotide. For example, if the SIS omits deoxyribo-adenine monophosphate, the first primering sequence-binding sequence also omits deoxyribo-adenine monophosphate. In this regard, if deoxyribo-adenine monophosphate is omitted from both the first primering sequence-binding sequence and strand identifier sequence, then dTTP and dUTP should be omitted from the polymerization conditions to synthesize a double-stranded SIS from a single-stranded SIS and a double-stranded first primering sequence-binding sequence from single-stranded first primering sequence-binding sequence.

The adaptors may also comprise a second primering sequence-binding sequence at least within the sequence of the adaptor being ligated to the 5' end of the fragmented double-stranded DNA. The second primering sequence-binding sequence may be 10 to 30 base pairs in length, more preferably 15 to 25 base pairs in length, more preferably still 18 to 23 base pairs in length. In some embodiments the second primering sequence-binding sequence may comprise the nucleotide omitted from the SIS. In some embodiments the second primering sequence-binding sequence may comprise the nucleotide omitted from the SIS and the nucleotide omitted from the first primering sequence-binding sequence. In some embodiments the second primering sequence-binding sequence may comprise the same nucleotide omitted from both the SIS and the first primering sequence-binding sequence.

Once ligated to the fragmented double-stranded DNA, the adaptor will comprise a 5' overhang. The 5' overhang is a single-stranded nucleotide sequence of variable numbers of base-pairs at the terminal end of the sequence of the adaptor ligated to the 5' end of the fragmented double-stranded DNA. Adaptors with a 5' overhang specifically exclude adaptors having a Y-adaptor structure where the 3' and 5' ends which are not ligated to the fragmented DNA are non-complementary and, thus, the adaptor forms a "Y" shape. The 5' overhang may comprise the second primering sequence-binding sequence. The 5' overhang may comprise from 5' to 3': the second primering sequence-binding sequence and the first primering sequence-binding sequence. The 5' overhang may comprise from 5' to 3': the second primering sequence-binding sequence, the first primering sequence-binding sequence, and the SIS.

Partial Polymerization

As noted above, the first primering sequence-binding sequence and the SISs of the adaptor may be in a single-stranded form and thus be a part of the 5' overhang of the ligated adaptor. However, it is contemplated that the fragmented DNA with the ligated adaptor will have the SIS and first primering sequence-binding sequence of each of the two adaptors on each of the two 3' ends of the fragmented DNA in addition to being on the 5' end of the fragmented DNA. That is, it is contemplated that the SIS and the first primering sequence-binding sequence of each of the two adaptors may be single-stranded or may be present in a double-stranded duplex. Consequently, if the first primering sequence-binding sequence and SIS are originally single-stranded and on the 5' ends of the fragmented DNA, then the information encoded in the SIS and first primering sequence-binding sequence will be transferred to the 3' ends of the fragmented DNA. They may be made double-stranded using the single-stranded first primering sequence-binding sequence and/or the single-stranded SIS as a template and having DNA polymerase synthesize a new strand from the closest free 3' end.

FIG. 2 illustrates in step "2.1" partial polymerization of the adaptors to make the SISs (labelled "SIS-1" and "SIS-2") on each end of the fragmented DNA (illustrated as "gDNA" or genomic DNA for illustrative purposes only). For reasons discussed further below, it may be desirable for the second primering sequence-binding sequence not to be on both the 5' and 3' ends of the fragmented DNA.

One means of accomplishing selective synthesis of a first primering sequence-binding sequence and SIS (or a reverse complement thereof) but not double-stranded blocking oligonucleotides is through a partial polymerization process. One non-limiting means of accomplishing partial polymerization is through the design of the single-stranded first primering sequence-binding sequences, the single-stranded SISs, and the single-stranded blocking oligonucleotide sequences. One non-limiting means of accomplishing partial polymerization via sequence design includes designing the single-stranded first primering sequence-binding sequences and the single-stranded SISs to exclude at least one nucleotide ("omitted nucleotide(s)") but then designing the second primering sequence-binding sequence to include at least one of the nucleotides omitted from the single-stranded first primering sequence-binding sequences and the single-stranded SISs. Then the polymerization conditions will be designed to stop elongation at the position in the 5' overhang of the adaptor where DNA polymerase reaches the nucleotide(s) included in the single-stranded second primering sequence-binding sequence but omitted from the single-stranded strand identifier sequence and the single-stranded first primering sequence-binding sequence.

One non-limiting means of designing the polymerization conditions would be to exclude from the polymerization conditions the dNTP which base-pairs to the omitted nucleotide ("omitted base-pairing dNTP"). When the DNA polymerase synthesizes the new strand of the first primering sequence-binding sequence and SIS, the DNA polymerase will be able to synthesize the full length of the first primering sequence-binding sequence and SIS. However, when the DNA polymerase continues down (in a 3' to 5' direction) the template strand to the single-stranded second primering sequence-binding sequence, it will eventually reach the nucleotide omitted from the first primering sequence-binding sequence and SIS in the second primering sequence-binding sequence. Because the polymerization conditions exclude or are free of the dNTP base-pairing to the omitted nucleotide, the DNA polymerase will not be able to insert a nucleotide to base-pair to the nucleotide(s) included in the single-stranded second primering sequence-binding sequence but omitted from the single-stranded strand identifier sequence and the single-stranded first primering sequence oligonucleotide sequence. The polymerization of the newly synthesized DNA will then stop at the first nucleotide included in the single-stranded second primering sequence-binding sequence but omitted from the single-stranded strand identifier sequence and the single-stranded first primering sequence oligonucleotide sequence. Because the full-length of the single-stranded template has not been made double-stranded, this synthesis is called partial polymerization or partially polymerizing, and is distinguishable from synthesis where the full length of the single-stranded template has been made double-stranded, which may be called polymerization, complete polymerization, full-length polymerization, polymerizing completely, etc.

In this regard, and with particular reference to FIG. 4, the star illustrates the location of the first omitted nucleotide immediately after the 5' end of the first primering sequence-binding sequence, b1. In certain embodiments, a sequence of nucleotides may be omitted or a nucleotide may be omitted in the context of an intervening sequence indicated b2. It is preferred that the first primering sequence-binding sequence omit a nucleotide and that the second primering sequence-binding sequence include the omitted nucleotide. In such an embodiment, it is further preferred that the omitted nucleotide be included as near as possible to the 3' end of the region b2 sequence (if present) andas close as possible to the 5' end of the first primering sequence-binding sequence, so that the DNA polymerase stops before the sequence of the second primering sequence-binding sequence, b3. Thus, little to none of the single-stranded second primering sequence-binding sequence would be made double-stranded when the omitted nucleotide is included as near as possible to, for example, the 3' end of the b2 sequence and/or before the sequence of the second primering sequence-binding sequence.

Although UMP or uracil is generally considered to replace TMP or thymidine in the genetic code as DNA is transcribed into RNA, deoxyribose uracil monophosphate (dUMP) has also been known to be used in place of dTMP in a DNA sequence.

In some embodiments, it is contemplated that a sequence of DNA, section of adaptor molecule, or oligonucleotide should omit or exclude one of the four classical DNA nucleotides, the four classical DNA nucleotides being dAMP, dCMP, dGMP, or dTMP. As dUMP and dTMP can under certain circumstances be used interchangeably in the genetic code, it is contemplated that if dTMP is to be excluded in a sequence of DNA, section of adaptor molecule, or oligonucleotide, then dUMP shall also be excluded and vice versa. In some embodiments, it is contemplated that a mix of components sufficient for the elongation of DNA from a primer ("an elongation mix") will exclude one or more types of DNA nucleotide(s) that base-pairs with the DNA nucleotide excluded from a sequence of DNA, section of adaptor molecule, or oligonucleotide. As dUTP can sometimes serve as a surrogate for dTTP (and dTTP can sometimes serve as a surrogate for dUTP), it is contemplated that if dTTP is to be excluded from the elongation mix, then dUTP shall also be excluded from the elongation mix and vice versa.

To provide an example of the foregoing, in one embodiment, the single-stranded strand identifier sequence and/or the first primering sequence-binding sequence will omit deoxyribo-adenine monophosphate, and the first nucleotide of the second primering sequence binding sequence (i.e. the first nucleotide at the 3' end within the b2 sequence will be a deoxyribo-adenine monophosphate). Within this example, the conditions giving rise to partial elongation would omit dTTP and dUTP but would include the other components normally required for full polymerization, such as DNA polymerase, buffers, concentrations of magnesium and/or calcium, etc. Within this example, the DNA polymerase would also be able to synthesize a new strand of DNA using as a template the single-stranded SIS and single-stranded first primering sequence-binding sequence. Within the single-stranded SIS and single-stranded first primering sequence-binding sequence, a dCTP would base-pair with a guanine in the template strand, a dGTP would base-pair with a cytosine in the template strand, and a dATP would base-pair with a thymidine in the template strand, and the single-stranded strand identifier sequence and single-stranded first primering sequence-binding sequence would be made double-stranded by DNA polymerase. However, when the DNA polymerase synthesizes the new strand of DNA in a 5' to 3' direction, it will read the template strand in a 3' to 5' direction, and it will eventually reach the first adenine in the first nucleotide position of the b2 sequence (i.e. the star in FIGS. 1 and 4 or the first position being the first nucleotide at the 3' end of the b2 sequence). Once the DNA polymerase reaches the adenine in the first position of the b2 sequence the DNA polymerization would stop at that adenine because the polymerization conditions lack dTTP and dUTP necessary to base-pair with the adenine. The adaptor sequences will, thus, only be partially polymerized. The adaptor, ligated to the fragmented DNA will still retain a 5' overhang which comprises the second primering sequence-binding sequence, b3, as well as the b2 sequence (if present), or a part thereof.

Once the SIS and first primering sequence-binding sequences of the ligated adaptors are made double-stranded but the second primering sequence-binding sequence is prevented from being made double-stranded via the partial polymerization process described above, the dual-adaptor ligated fragmented DNA may be denatured to obtain at least one single-stranded DNA template.

In some embodiments it is preferable that the single-stranded DNA template comprise the single-stranded fragmented DNA and two SISs, one SIS being at each end of the single-stranded fragmented DNA. In some embodiments it is preferable that the single-stranded DNA template comprise the single-stranded fragmented DNA, two SISs, and two primering sequence-binding sequences, one SIS and one primering sequence-binding sequence being at each end of the single-stranded fragmented DNA. In some embodiments it is preferable that the single-stranded DNA template comprise the single-stranded fragmented DNA, two SISs, two primering sequence-binding sequences, and one blocking-oligonucleotide binding sequence, one SIS and a first primering sequence-binding sequence being at each end of the single-stranded fragmented DNA but the second primering sequence-binding sequence being at the 5' end of the adaptor ligated fragmented DNA but not at the 3' end of the adaptor ligated fragmented DNA.

Denaturing

As noted above, in preferred embodiments, the SIS and the first primering sequence-binding sequence but not the second primering sequence-binding sequence should be present in a double-stranded duplex at ligation or be made double-stranded by partial polymerization after ligation. In either event, the result would be a double-stranded template each strand comprising working from 3' to 5': a first primering sequence-binding sequence, an SIS, an optional intervening nucleotide sequence, a DNA fragment to be analyzed, another optional intervening nucleotide sequence, another (different) SIS, and then and finally a second primering sequence-binding sequence. At this point, the double-stranded template may be denatured or deannealed to obtain a single-stranded template. FIG. 2 illustrates in step "2.2" the denaturing of the single-stranded template.

Denaturing may include but is not limited to increasing the temperature of the adapted double-stranded DNA preferably near the annealing temperature of the double-stranded DNA or more preferably above the annealing temperature of the double-stranded DNA, or more preferably still 5° C. above the annealing temperature of the double-stranded DNA. It is generally understood that the annealing temperature of a double-stranded DNA can be calculated from known references and computer programs which are largely based off of the work of Ignacio Tinoco Jr, Kenneth Sauer, and/or James C Wang which was published in several manuscripts and books, including IGNATIO TINOCO JR. KENNETH SAUER, AND JAMES C. WANG PHYSICAL CHEMISTRY: PRINCIPLES AND APPLICATIONS IN BIOLOGICAL SCIENCES 165-167 ($3^{rd}$ ed. 1995), which is hereby incorporated by reference. See also Breslauer et al. 83 PROC. NATL. ACAD. SCI. 3746, also hereby incorporated by reference. In this regard, the melting/annealing temperature of the double-stranded DNA is calculated by determining the Gibbs free energy of the double-stranded DNA and then calculating the temperature at which 50% of the DNA will be in a double-stranded form and 50% will be in a single-stranded form.

The annealing/melting temperature is dependent on the length of the double-stranded DNA, such that the annealing/melting temperature increases with increasing length of double-stranded DNA. For example, generally an 18 base pair length of double-stranded DNA will have a lower annealing/melting temperature than a 30 base-pair length of double-stranded DNA. The annealing/melting temperature is also dependent on the relative guanine/cytosine to adenine/thymidine content of the double-stranded DNA. For example, adenine forms two hydrogen bonds with each thymidine in double-stranded DNA whereas guanine forms three hydrogen bonds with each cytosine in double-stranded DNA. The annealing/melting temperature generally increases with increasing numbers of hydrogen bonds. Therefore, a sequence consisting of guanine and cytosine will have a higher melting temperature than a sequence of equal length consisting of adenine and thymidine. However, because the double-stranded DNA includes the fragmented DNA, whose sequence is unknown, it is generally preferred to increase the temperature of the double-stranded DNA to a temperature from 95° C. to 100° C. In general, all double-stranded DNA will have an annealing/melting temperature less than 95° C. under physiological and/or typical in vitro conditions used for molecular biology. Therefore, in general DNA of all lengths and all relative guanine/cytosine to adenine/thymidine content will be melted or denatured at a temperature from 95° C. to 100° C.

Denaturing may include but is not limited to adding helicase (also known as DNA helicase, DnaB protein) to unwind or unzip the adapted double-stranded DNA. The term "denaturing" has also been used, less commonly to mean the complete digestion of DNA into nucleotides via, for example, an exonuclease or enzyme with exonuclease activity. Exonucleases cleave nucleotides, one at a time, from the end (exo) of a polynucleotide or oligonucleotide, for example, by hydrolyzing the phosphodiester bonds at either the 3' or 5' ends of the nucleotide or polynucleotide. DNA polymerase I has 3' to 5' and 5' to 3' exonuclease activity which can confer proofreading activity. Unless otherwise specified, "denaturing" refers to the separation of a double-stranded oligonucleotide or polynucleotide into two single-stranded oligonucleotides or polynucleotides by breaking the hydrogen bonds of the base-paired nucleotides but not by means of breaking the phosphate-sugar backbone of the oligonucleotide or polynucleotide or the links between the bases (adenine, guanine, cytosine, thymidine, uracil) and the backbone. In this regard, unless otherwise specified, "deannealing" and "denaturing" are synonymous. And, thus, "denaturing" unless otherwise specified excludes complete digestion of DNA into nucleotides, via, for example, an exonuclease or enzyme with exonuclease activity.

Annealing the First PS and, Optionally, a Blocking Oligonucleotide

Once a single-stranded template has been obtained, a first primering sequence and, optionally, a blocking oligonucleotide may be annealed, in no particular order, to at least one of the two single-stranded templates. In preferred embodiments, the first primering sequence and, optionally, a blocking oligonucleotide may be annealed, in no particular order, to each of the two single-stranded templates. In a preferred embodiment, the first primering sequence and the blocking oligonucleotide are to be annealed, in no particular order, to at least one of the two single-stranded templates. In more preferred embodiments, the first primering sequence and the blocking oligonucleotide are annealed, in no particular order, to each of the two single-stranded templates. In a preferred embodiment, the blocking oligonucleotide is annealed before the first primering sequence is annealed to at least one of the two single-stranded templates. In more preferred embodiments, the blocking oligonucleotide is annealed to each of the two single-stranded templates before the first primering sequence is annealed to each of the two single-stranded templates. FIG. 2 illustrates in step "2.2" the annealing of the first-primer (labeled as "PS-1") and the blocking oligonucleotide to the single-stranded template.

Annealing of the first primering sequence and, optionally, the blocking oligonucleotide to both of the single-stranded templates may enable later analysis of the sequenced fragmented DNA by duplex-seq, and is preferable because the annealing of the first primering sequence will be used for first-strand synthesis. As a practical consideration, because the first primering sequence-binding sequence on the 3' end of each of the single-stranded templates will be the same, and because the second primering sequence-binding sequence on the 5' end of each of the single-stranded templates will be the same, it is likely that the first primering sequence and the blocking oligonucleotide will anneal to each of the two single-stranded template.

The First Primering Sequence

In some embodiments, the primering sequences, including the first primering sequence and the second primering sequence, will anneal to the 3' terminus of the template strand to ensure complete replication of the template strand. In some embodiments, the primering sequence comprises a sequence which anneals to the 3' terminus of the template strand and also comprises a 5' overhang, the 5' overhang comprising additional nucleotide sequences. When the primering sequence comprising the 5' overhang and 3' terminus annealing sequence is elongated, the newly synthesized strand will not only incorporate all the genetic information of the template strand but will also include the nucleotide sequence of the primering sequence, including the 5' overhang of the primering sequence, thus incorporating the genetic information and/or functional characteristics of the overhang, into the daughter strand not found in the template strand.

In preferred embodiments, the first primering sequence may anneal to the first primering sequence-binding sequence on the 3' end of the single-stranded template. The first primering sequence is not particularly limited so long as it anneals to the 3' end of the single-stranded template and it has a free 3'-OH permitting elongation. The first primering sequence may have a sequence which is partially complementary to the first primering sequence-binding sequence, or more preferably, the first primering sequence may have a sequence that is fully complementary to the first primering sequence-binding sequence. FIG. 4, the sequence b1 illustrates the first primering sequence-binding sequence of the adaptors, and the sequence of the first primering sequence which anneals to the first primering sequence-binding sequence will have high homology. High homology being homology sufficient to permit annealing. The first primering sequence may have an additional sequence which binds to the sequence of the adaptor sequence outside of the first primering sequence-binding sequence, including for example, the SISs. However, since the SISs may be random or near random sequences, such binding of the first primering sequence to the SISs should be rare. Using FIG. 4 for reference, it is noted that the blocking-oligonucleotide binding sequence of the adaptors may comprise sequences spanning the b1, b2, and b3 sequences or portions thereof and may not necessarily include any part of one or more of the b1, b2, or b3 sequences. The sequence of the first primering sequence opposite b3 sequence may have low homology to the b3 sequence.

Because the first primering sequence-binding sequence of the adaptors may omit one or more nucleotides, it is contemplated that in some embodiments, the first primering sequence omits the nucleotide which base-pairs to the first primering sequence-binding sequence in at least the sequence of the first primering sequence which anneals to the first primering sequence-binding sequence. For example, if the first primering sequence-binding sequence of the adaptor omits adenine, and the sequence of the first primering sequence which anneals to the first primering sequence-binding sequence is fully complementary to the first primering sequence-binding sequence, then the sequence of the first primering sequence which anneals to the first primering sequence-binding sequence will omit thymidine and uracil from the sequence. In this example, however, sequences of the first primering sequence (other than the sequence which anneals to the first primering sequence-binding sequence) may still comprise the nucleotide omitted from the sequence of the first primering sequence which anneals to the first primering sequence-binding sequence.

In this regard, if the sequence of the first primering sequence which anneals to the first primering sequence-binding sequence is fully complementary, it is worthwhile noting the arrangement of the sequence of the first primering sequence which anneals to and is complementary with the first primering sequence-binding sequence, particularly when there is a partial polymerization used to form a double-stranded first primering sequence-binding sequence after ligation of the adaptors. Assuming for illustrative purposes that the first primering sequence-binding sequence is "b1", and assuming that the partial polymerization forms a new strand of the first primering sequence-binding sequence, which is now complementary to b1, said complementary sequence being "b1 prime" (wherein "prime" indicates complementarity to b1), and assuming that the first primering sequence anneals to the first primering sequence-binding sequence when the first primering sequence-binding sequence is at the 3' end of the single-stranded template, then the sequence of the first primering sequence which anneals to the first primering sequence-binding sequence will have a sequence which is the same as that of b1 when fully complementary to "b1 prime" of the first primering sequence-binding sequence.

Optional 5' Overhang of the First Primering Sequence

In preferred embodiments, the first primering sequence may comprise additional sequences in a 5' direction from the sequence which binds to the first primering sequence-binding sequence. Thus, when annealed to the first primering sequence-binding sequence, the first primering sequence will comprise sequences that "over-hang" the 3' end of the single-stranded template. For convenience, these additional sequences in a 5' direction from the sequence of the first primering sequence which binds to the first primering sequence-binding sequence will be known as the "5' overhang sequence of the first primering sequence." This overhang sequence may comprise an index sequence, a first sequencing sequence, and/or a first immobilizing sequence.

First Primering Sequence May Comprise an Index Sequence

The index sequence is a sequence of nucleotides of sufficient length with which to provide enough permutations of index sequences to identify the source of a sample of DNA individually or in combination with another index sequence. An index sequence may be at least 2 nucleotides, preferably 4 to 20 nucleotides, and more preferably 4 to 12 nucleotides. For example, assuming a study comprises DNA from 16 different sources, a sequence of 2 nucleotides may be sufficient to identify all 16 samples (4×4=16, assuming all four nucleotides are used: A, T, G, and C). FIG. 1 illustrates one possible location of the index sequences (labelled as "IS-1" and "IS-2") on primers. The index sequence may contain the nucleotide omitted from the SIS and/or the first primering sequence-binding sequence. The index sequence may omit the nucleotide omitted from the SIS and/or the first primering sequence-binding sequence.

The index sequence is a designed sequence used to identify, individually or in combination with a second index sequence, a particular source from which the sample of DNA (being fragmented, ligated with an adaptor, and sequenced) was taken. The source from which the sample of DNA may be an individual (also known as a subject) or one of several locations within an individual (such as tissue that could possibly be cancerous). An index is a sequence used for downstream sorting and identification of the source from which the DNA of the sample of the DNA after the sequencing of the DNA. The index may also be known as a barcode or a tag. When there are DNAs from more than one source being sequenced at the same time (also known as multiplexing), the indexes are later identified by bioinformatics software and used to sort or attribute the DNA sequence reads from all the sources into each particular source. Multiplexing may be used in conjunction with duplex-seq, wherein after sorting of DNA sequence reads into each particular source via the index sequence, any genetic mutations within one or several cells from that source may be identified. The number of nucleotides in the index sequence (the length of the index sequence) can be scaled up or down depending on the number of sources from which DNA is taken. Assuming for example, there are two nucleotides in the index sequence, each of the two positions of the nucleotides possibly being represented by adenine, guanine, cytosine, thymidine (or in thymidine's place uracil), then up to 16 samples may be sequenced (4 possible combinations of nucleotides in the first position of the index sequence multiplied by 4 possible combinations of nucleotides in the second position of the index sequence).

It is further described below that there is a first-primer which may comprise a first index sequence and a second-primer which may comprise a second index sequence. Each of the first and second index sequences may have the same or different properties but preferably they may have a different sequence of nucleotides in the index sequence. The second primering sequence will be annealed to the end of single-stranded template opposite the end to which the first primering sequence has been annealed (and extended or elongated). Thus, the source of each fragmented double-stranded DNA can be identified by each of the index sequences, possibly by each of the index sequences individually, or possibly by the combination of the two first and second index sequences.

The first and second index sequences may be previously determined sequences used to identify the source of the DNA sequence and are not particularly limited. The first and second index sequences may be of sufficient length to provide enough permutations of first and second index sequences to identify each and every source of DNA in combination with the other index sequence of the other primer annealed to the end of the single-stranded template. The first and second index sequences may be random sequences or near random sequences (provided the specific sequence may be determined for each sample). By random, it is meant that it is possible in the synthesis of a index sequence, each nucleotide is chosen independently of the previous nucleotide in the sequence. For example, each of the four nucleotides (deoxyribo-adenine monophosphate, deoxyribo-cytosine deoxyribose monophosphate, deoxyribo-guanine monophosphate, and deoxyribo-thymidine monophosphate) would be as likely as the next to be chosen (25% probability) after the selection of the nucleotide prior in the sequence. By near random, it is understood that the conditions determining the next nucleotide in the sequence, including the enzymes determining the next nucleotide in the sequence, may not be fully independent but instead close to independent. For example, one nucleotide, a thymidine, might have a slightly higher probability of being selected, a 25.5% chance, when the previous nucleotide selected in the sequence is also a thymidine. By near random it is understood that for example, after random selection of three adenines in a row, the nucleotide mix might be depleted of adenines, making the selection of thymidine, guanine, or cytosine more likely than adenine.

The First Primering Sequence May Comprise an Immobilizing Sequence and a Sequencing Sequence An immobilizing sequence may function similarly to a universal first end, as in U.S. Pat. No. 7,985,565, and/or a first-flow-cell recognition sequence. A first immobilizing sequence may be designed with a sequence that anneals to a first immobilizer sequence. As described further, the first immobilizing sequence may be bound at the 5' end to a solid-state support. Hence, when the first immobilizing sequence anneals to the first immobilizer sequence, a DNA strand comprising the first immobilizing sequence will be immobilized by the immobilizer sequence bound to the solid-state support.

A first sequencing sequence, if included in the first primering sequence, may anneal to a first sequencing primer. In certain embodiments, the first sequencing primer initiates the elongation of the fragmented DNA during sequencing by synthesis. Once the first sequencing primer is annealed and is being elongated during sequencing-by-synthesis, the machine performing the sequencing by synthesis will detect the incorporation of each nucleotide into the newly synthesized strand of DNA, thus sequencing the template strand of fragmented DNA by the order in which nucleotides are newly incorporated into the daughter strand of DNA. The first sequencing sequence may omit the nucleotide omitted from the SIS and/or the first primering sequence-binding sequence. If omitted, the first sequencing primer which anneals to the first sequencing sequence may in turn omit the nucleotide which base-pairs to the nucleotide omitted from the first sequencing sequence.

Other Modifications to the First Primering Sequence

The first primering sequence may contain sequences and chemical modifications, including but not limited to those that will facilitate their use for multiple downstream sequencing approaches. For example, the first primering sequence may contain restriction sites or homing endonuclease sites to facilitate the downstream addition of custom adaptors at both ends, including Y shaped DNA adaptors, or DNA hairpins. The first primering sequence may contain sequence to facilitate the attachment to a solid matrix such as a surface (e.g., flow-cell), lipid bilayer or a bead. The primering sequence may contain sequences or modifications to facilitate the attachment of the nucleic acid molecule to a lipid membrane or bilayer. Typical modifications to attach a sequence to a lipid membrane include, but are not limited to, thiol, biotine, cholesterol, tocopherol or surfactants (e.g., lipids, palmitate . . . ). The primering sequence may contain sequences complementary to a nucleotide attached to a lipid bilayer. The primering sequence may contain also elements to facilitate the interaction with DNA or RNA polymerases, helicases, ribosomes, transmembrane pores or exonucleases such as the ones used in stochastic or single molecule nucleic acid sequencing approaches.

The primering sequence may contain sequences to facilitate the attachment of a nucleic acid sequence forming a hairpin loop, which may allow the covalent linkage of the two strands in a double stranded nucleic acid template. The presence of a hairpin loop attached to the primering sequence may allow to link covalently both strands of the nucleic acid template and delineate (divide) both strands in the double stranded nucleic acid template. Accordingly, this may allow sequencing consecutively both strands of a double stranded nucleic acid molecule that may be delimited by the sequence of the sequence of the hairpin loop. Sequencing both strands of the same molecule may increase the sequencing quality. A hairpin loop may be also present at both sides of a template generating a closed circular nucleic acid molecule formed by an internal double stranded nucleic acid template delimited by two hairpin loops (dumbbell shape). That would allow multiple consecutive cycles sequencing the template, hairpin loop 1, reverse complement to the template and hairpin 2. The generation of this closed nucleic acid dumbbell molecule may allow the amplification of the molecule by a DNA or RNA polymerase with strand displacement or 5'-3'exonuclease activity.

In such an embodiment, molecular biology techniques may be employed such as rolling circle amplification using the Phi29 DNA polymerase, or DNA sequencing of concatemers of copies of sense and antisense strands as in U.S. Pat. No. 9,910,956, which is hereby incorporated by reference. Sequencing of concatemer copies of the sense and antisense strand of the same molecule may allow to increase sequencing quality by generating a circular consensus molecule of the original nucleic acid insert. The sequences present in first primering sequence might allow the use of bridge amplification by the presence of complementary oligonucleotides attached to a surface. The sequences present in first primering sequence might also allow the use of water in oil based emulsion PCR amplification and attachment to beads. The first primering sequence may contain sequences allowing for the formation of DNA concatemers to facilitate the sequencing of long stretches of DNA. The sequences present in the first primering sequence might facilitate the targeting to exonucleases used in exonuclease sequencing. The sequences present in the first primering sequence might facilitate targeting to nanopores used in nanopore sequencing. The first primering sequence may also comprise modifications such as biotin, digoxigenin, thyol modified nucleotides, click-chemistry or any other reactive group that facilitates their binding to a solid support or lipid membrane with complementary chemistry.

Orientation of the First Primering Sequence to the Adaptor Ligated Fragmented DNA When the first primering sequence comprises a sequence which anneals to the first primering sequence-binding sequence, a first index sequence, and a first immobilizing sequence, it is preferred that the order of the sequences be as follows from 3' to 5': the first primering sequence-binding sequence, the first index sequence, and the first immobilizing sequence.

As noted above, it is preferred that the first primering sequence anneal to the first primering sequence-binding sequence on the 3' end of the single-stranded template but not to the 5' end of the single-stranded template. As noted above, the adaptors will anneal to the 5' end of the double-stranded DNA fragment. Also as noted above, if the first primering sequence-binding sequence of the adaptor, as ligated to the 5' end of the double-stranded DNA fragment, is sequence "b1", and if the first primering sequence anneals to the 3' end of the double-stranded DNA, then the first primering sequence-binding sequence which is annealed will be "b1 prime" and the sequence of the first primering sequence which anneals to the first primering sequence-binding sequence will be sequence "b1". Therefore, since the first primering sequence has the same sequence "b1" as the first primering sequence-binding sequence "b1" on the 5' end of the single-stranded template, the first primering sequence will not anneal to the 5' end of the single-stranded DNA. Consequently, when both the blocking oligonucleotide and the first primering sequence are included in the embodiment, the order of annealing to the single-stranded sequence is not particularly limited. For example, the blocking oligonucleotide may anneal first, then the first primering sequence may anneal second, or the first primering sequence may anneal first and the blocking oligonucleotide may anneal second, or the first primering sequence and blocking oligonucleotide may anneal at the same time.

The Blocking Oligonucleotide Sequence

In embodiments, including the blocking oligonucleotide and/or an adaptor with a second primering sequence-binding sequence, it is preferred that both be included. In some embodiments, the blocking oligonucleotide may anneal not only to the second primering sequence-binding sequence, but also to the first primering sequence-binding sequence. In this regard, the blocking oligonucleotide may anneal to the omitted nucleotide. For example, FIG. 4 shows the blocking oligonucleotide annealing to region b1 (the first primering sequence-binding sequence), b2 (the first incidence in the 3' to 5' direction of the nucleotide omitted from the strand identifier sequence and the first primering sequence-binding sequence), and part of b3. In the example immediately above, when annealing to the first primering sequence-binding sequence it would be annealing to the "b1" sequence of the first-binding sequence on the 5' end of the single-stranded template, and therefore the blocking oligonucleotide may not interfere with the first primering sequence-binding to the "b1 prime" sequence on the 3' end of the single-stranded template to which the first primering sequence is bound. In this regard, if the adaptor as annealed to the 5' end of the double-stranded DNA fragment includes a second primering sequence-binding sequence, said sequence being at least "b3", and if the blocking oligonucleotide is fully complementary to the second primering sequence-binding sequence, then the blocking oligonucleotide will have a sequence of "b3 prime" (with "prime" indicating full complementarity). Thus, even if the second primering sequence-binding sequence is made double-stranded, such as by partial polymerization or full polymerization, such that the 3' end of the adaptor (ligated to DNA or not ligated to DNA) comprises a second primering sequence-binding sequence, the second primering sequence-binding sequence will be or be made at least "b3 prime". Thus, the blocking oligonucleotide having a sequence of "b3 prime" will not bind to the second primering sequence-binding sequence on the 3' end of the adaptor because it is also "b3 prime". However, the "b3 prime" second primering sequence-binding sequence on the 3' end of the adaptor may interfere with the binding of the first primering sequence (having an "b1" sequence) to the first primering sequence-binding sequence (having an "b1-prime") on the 3' end of the single-stranded template due to some steric interference created by having the 5' overhang of the first primering sequence not annealing to the "b3 prime" sequence of the second primering sequence-binding sequence. Thus, is preferable that the second primering sequence-binding sequence not be made or not be double-stranded.

The blocking oligonucleotide may thus be optional, and may be used to prevent the formation of hairpins in the ligated adaptors on the template strand and/or the binding of a 5' end of a single-stranded template to the 3' end of another single-stranded template and subsequent elongation to create a product with two separate sequences of fragmented DNA. Alternatively, the blocking oligonucleotide may be used to prevent the early binding of the second primering sequence before a product has been elongated (i.e. polymerized, synthesized, or made) from the annealing of the first primering sequence to the single-stranded template (i.e. either the extension of the 3' end of the single-stranded template or the extension of the 3' end of the first primering sequence). For example, disclosed below is an optional approach of adding the dNTP which base-pairs to the nucleotide omitted from the SIS and/or the first primering sequence-binding sequence in order to create conditions allowing for extension of a partially polymerized product into a product that elongates the 3' end of the adaptor to replicate the 5' overhang of the first primering sequence, and/or elongates the 3' end of the first primering sequence to replicate the 3' SIS, the fragmented DNA and preferably the adaptor at the 5' end of the singe-stranded template, including preferably the strand identifier sequence, the first primering sequence-binding sequence, and second primering sequence-binding sequence of the adaptor at the 5' end of the singe-stranded template. In this optional approach, the second-primer may be added when adding the dNTP which base-pairs to the nucleotide omitted from the SIS and/or the first primering sequence-binding sequence. In this optional approach, the blocking oligonucleotide will be annealed to the 5' end of the single-stranded template, and will therefore prevent the second primering sequence from annealing to this sequence and potentially causing a second competing polymerization reaction until such time as a full-length product may be obtained from the removal of the blocking oligonucleotide and completion of the polymerization reaction involving the first primering sequence.

The blocking oligonucleotide may also be optionally used to prevent primer-dimer formation and elongation and other non-specific products created by unligated adaptor molecules annealing to each other and being elongated.

In this regard, if the blocking oligonucleotide is to be used, it may be added in an excess amount or concentration. The excess amount or concentration may depend upon the amount or concentration of single-stranded template, first primering sequence, and second primering sequence. The amount or concentration of first primering sequence and second primering sequence may also depend on the amount or concentration of single-stranded template. It is preferred that the final concentration of first primering sequence in the admixture be from 1 nM to 20 µM, more preferably may be from 100 nM to 5 µM, more preferably still may be from 500 nM to 2 µM, and more preferably still 1 µM It is preferred that the final concentration of the second primering sequence be from 1 nM to 20 µM, more preferably from 100 nM to 5 µM, more preferably still from 500 nM to 2 µM, and more preferably still 1 µM. Because the amount of blocking oligonucleotide may depend upon the amount of first and second primering sequence, a practitioner should generally consider the blocking oligonucleotide be admixed such that the final concentration of blocking oligonucleotide be the same as the first and second primering sequences. Alternatively, the final concentration of the blocking oligonucleotide may be less than or greater than the final concentration of the first and second primering sequences. For example, the final concentration of the blocking oligonucleotide 3 times as much as the first primering sequence.

Blocking Oligonucleotide Melting/Annealing Temperature

In some embodiments, it is preferred that the blocking oligonucleotide have an annealing temperature equal to or slightly higher than the temperature at which the first primering sequence anneals. It is generally understood that the annealing temperature of a primer, polynucleotide, or oligonucleotide, including for example, the first primering sequence, the second primering sequence, the immobilizer sequence, the second immobilizer sequence, and the blocking oligonucleotide, can be calculated from known references and computer programs which are largely based off of the work of Ignacio Tinoco Jr, Kenneth Sauer, and/or James C Wang which was published in several manuscripts and books, including IGNATIO TINOCO JR. KENNETH SAUER, AND JAMES C. WANG PHYSICAL CHEMISTRY: PRINCIPLES AND APPLICATIONS IN BIOLOGICAL SCIENCES at 165-167 ($3^{rd}$ ed. 1995), which is hereby incorporated by reference. See also Breslauer et al. 83 PROC. NATL. ACAD. SCI. 3746, also hereby incorporated by reference. In this regard, the melting/annealing temperature of the double-stranded DNA is calculated by determining the Gibbs free energy of the double-stranded DNA and then calculating the temperature at which 50% of the DNA will be in a double-stranded form and 50% will be in a single-stranded form.

The annealing/melting temperature of a primer, polynucleotide, and/or oligonucleotide once it has formed a duplex with another polynucleotide, oligonucleotide, or length of DNA is dependent on the length of the nucleotide sequence, such that the annealing/melting temperature increases with increasing length of the nucleotide sequence. For example, generally an 18 base pair length of duplex will have a lower annealing/melting temperature than a 30 base-pair length of annealed and therefore duplex. The annealing/melting temperature of the duplex is also dependent on the relative guanine/cytosine to adenine/thymidine content of the duplex. For example, adenine forms two hydrogen bonds with each thymidine in double-stranded DNA whereas guanine forms three hydrogen bonds with each cytosine in double-stranded DNA. The annealing/melting temperature of the duplex generally increases with increasing numbers of hydrogen bonds. Therefore, a sequence consisting of guanine and cytosine will have a higher melting temperature than a sequence of equal length consisting of adenine and thymidine. The annealing/melting temperature of a duplex is also dependent on the relative amount of complementarity, whether determined by Watson-Crick base-pairing or non-Watson-Crick base-pairing. For example, a duplex with a one mismatch, a number of mismatches, one stretch of mismatches, or several stretches of mismatches will have a lower melting temperature than a duplex of the same length that is fully complementary wherein the sequence is comprised entirely of Watson-Crick base-pairing nucleotides. For example, a sequence with some wobble base-pairing (non-Watson-Crick base-pairs) will have a lower melting temperature than a duplex of the same length that is fully complementary and wherein the sequence is comprised entirely of Watson-Crick base-pairing nucleotides.

Therefore, in some embodiments, the blocking oligonucleotide has a greater number of nucleotides in its sequence that anneals to the single-stranded template than that of the sequence of the first primering sequence which anneals to the single-stranded template. In some embodiments, the blocking oligonucleotide has a greater relative amount of guanine and cytosine content relative to adenine and thymidine content in its sequence that anneals to the single-stranded template than that of the sequence of the first primering sequence which anneals to the single-stranded template. For example, the blocking oligonucleotide may have a 60% guanine and/or cytosine relative content in its sequence that anneals to the single-stranded template and the sequence of the first primering sequence which anneals to the single-stranded template may have a 40% guanine and/or cytosine relative content. As noted above, several programs are available which can be used to design primers, and which can also be used to design the annealing sequences of the blocking oligonucleotide and first primering sequence to the single-stranded template. These programs allow the practitioner to set the intended annealing temperature, intended length, and intended relative content of guanine and cytosine in order to design an oligonucleotide. As such, these parameters may be set for designing a blocking oligonucleotide, first primering sequence, and even a second primering sequence such that the blocking oligonucleotide has an annealing temperature with the single-stranded template similar to or greater than the annealing temperature of the first primering sequence to the single-stranded template. By similar, it is meant that the annealing temperatures of the first primering sequence and blocking oligonucleotide to the single-stranded template are within 4° C. of one another.

In some embodiments, it is preferred that the blocking oligonucleotide have an annealing temperature equal to or higher than the temperature at which one end of the template may anneal to the other end of the template. In a preferred embodiment, the blocking oligonucleotide may have an annealing temperature equal to or higher than the temperature at which the end of the template that binds to the first primering sequence anneals to the other end of the template that binds to the blocking oligonucleotide sequence.

In some embodiments, it is preferred that the blocking oligonucleotide and first primering sequence have annealing temperatures to the single-stranded template below 62° C. In some embodiments, it is preferred that the blocking oligonucleotide and first primering sequence have annealing temperatures to the single-stranded template from 45° C. to 62° C. In some embodiments, it is preferred that the blocking oligonucleotide and first primering sequence have annealing temperatures below 58° C. In some embodiments, it is preferred that the blocking oligonucleotide and first primering sequence have annealing temperatures to the single-stranded template from 45° C. to 58° C. In some embodiments it is preferred that the blocking oligonucleotide and first primering sequence have annealing temperatures from 55 to 58° C. In some embodiments, it is preferred that the blocking oligonucleotide and first primering sequence have annealing temperatures below 50° C. In some embodiments, it is preferred that the blocking oligonucleotide and first primering sequence have annealing temperatures to the single-stranded template from 45° C. to 50° C.

In some embodiments, the actual temperature setting for the annealing of the first primering sequence and optionally the blocking oligonucleotide may be lower than the annealing temperature of the first primering sequence and blocking oligonucleotide. That is, the annealing temperature of the first primering sequence, as defined above, is the temperature at which 50% of the first primering sequence is bound to the single-stranded template and is determined by the Gibb's Free Energy of the association between the two strands. And that is, the annealing temperature of the blocking oligonucleotide, as defined above, is the temperature at which 50% of the blocking oligonucleotide is bound to the single-stranded template and is determined by the Gibb's Free Energy of the association between the two strands. In order to have more than 50% binding of either the first primering sequence or blocking oligonucleotide, it is preferable that the actual temperature of the single-stranded template, first primering sequence, and, optionally, the blocking oligonucleotide mixture be lower than the annealing temperature of the first primering sequence and/or blocking oligonucleotide (this is referred to as the actual temperature of annealing). For example, the actual temperature of annealing may be 5° C. than the annealing temperature of the first primering sequence and optionally the blocking oligonucleotide.

In some embodiments, it is preferred that 95% of the single-template be annealed to a first primering sequence and optionally, the blocking oligonucleotide at 48° C. In some embodiments, it is preferred that 99% of the single-template be annealed to a first primering sequence and optionally, the blocking oligonucleotide at 48° C. In some embodiments, it is preferred that 99.9% of the single-template be annealed to a first primering sequence and optionally, the blocking oligonucleotide at 48° C. In some embodiments, it is preferred that 99.99% of the single-template be annealed to a first primering sequence and optionally, the blocking oligonucleotide at 48° C. In some embodiments, it is preferred that 99.999% of the single-template be annealed to a first primering sequence and optionally, the blocking oligonucleotide at 48° C. In some embodiments, it is preferred that all of the single-template be annealed to a first primering sequence and optionally, the blocking oligonucleotide at 48° C.

After the first primering sequence and optionally the blocking oligonucleotide have been annealed to the single-stranded template, the single-stranded template and/or the first primering sequence may be elongated (e.g. the 3' ends extended via polymerization through semi-conservative replication), wherein the elongation may be complete elongation or polymerization and/or through an initial partial elongation or polymerization extending the lengths of the 3' ends followed by complete elongation or polymerization. As noted above, the blocking oligonucleotide may be removed from the single-stranded template to effectuate complete elongation, particularly when a DNA polymerase without exonuclease activity has been used.

Partial and/or Complete Elongation for First Strand Synthesis

If the adaptors were not previously elongated via partial elongation as described above, an elongation mixture may be added after the first primering sequence and optionally the blocking oligonucleotide have been annealed to the single-stranded template. In this example, the elongation mixture may be either a mixture for complete elongation or a mixture for partial elongation. If the adaptors were previously elongated via partial elongation as described above, the previously added partial elongation mixture may suffice for elongation of the first primering sequence and/or single-stranded template. In this event, the partial polymerization will occur immediately after the annealing of the first primering sequence to the first primering sequence-binding sequence potentially without any changes to the reaction conditions. FIG. 2 illustrates in step "2.2" how the annealing of the first-primer (labeled as "PS-1") and the blocking oligonucleotide to the single-stranded template will proceed immediately to the partial elongation in the event there was an earlier partial elongation of the SISs and first primering sequence-binding sequence. However, it is also contemplated that the practitioner may add further reactants for partial elongation, particularly if the practitioner believes that the reactants may have been depleted earlier. For example, if the partial polymerization of the adaptors occurred earlier and these conditions omitted dTTP and dUTP (because deoxyribo-adenine monophosphate was omitted from the SIS), then dATP, dGTP, and dCTP but not dTTP and dUTP may be added to replenish depleted dATP, dGTP, and dCTP. Likewise, if a thermolabile DNA polymerase was used to elongate the adaptors, then DNA polymerase may be replenished.

During the partial elongation, the first primering sequence may be elongated to replicate the strand identifier sequence on the 3' end of the single-stranded template, and/or some of the single-stranded template may be elongated to replicate some of the 5' overhang sequence of the first primering sequence. The partial elongation conditions are not particularly limited, and may be carried out, for example, at the actual temperature of annealing at which the first primering sequence and optionally the blocking oligonucleotide bound to the single-stranded template, or they may occur at a lower temperature. For example, if the actual temperature of annealing was set to 48° C. then the setting for the partial elongation temperature may be 48° C. Generally a lower temperature is not preferred as this will decrease the efficiency and speed at which DNA polymerase synthesizes new strands. Because nucleotides are being added to the first primering sequence and/or single-stranded template, it is possible to increase that temperature during the partial polymerization step because the newly synthesized sequence will increase the annealing temperature between the two strands.

At some point during the polymerization process, DNA polymerase will hit a nucleotide in the strand being used for a template to make a new strand and for which there is not an available dNTP which would base-pair to the nucleotide. This nucleotide would be the nucleotide omitted from the SIS, but would be one that could be included, for example, in the fragmented DNA or in the 5' overhang of the first primering sequence. At this point, a complete elongation reaction mixture should be provided.

Complete Elongation

Complete elongation may be initiated without prior partial polymerization, particularly when the ligated adaptors already comprise a double-stranded SIS and a double-stranded first primering sequence-binding sequence. Alternatively, complete elongation may be initiated by adding at least the oligonucleotide omitted from the partial elongation reaction mixture. For example, if dATP is omitted from the partial elongation reaction mixture (because the strand identifier sequence and/or the first primering sequence-binding sequence omit thymidine and/or uracil or deoxyribo-thymidine monophosphate and/or deoxyribo-uracil monophosphate), then at least dATP may be added at this time. FIG. 2 illustrates in step "3" the elongation of the first-primer (labeled as "PS-1") and the single-stranded template to make a double-stranded product. However, as noted above, it is possible that the dNTPs used in the partial elongation mixture may be depleted, it is also embodied that in addition to the addition of the omitted dNTP that other dNTPs also be added to initiate complete elongation. For example, in addition dATP being added to initiate complete elongation because it was omitted from the partial elongation mixture and in turn because deoxyribo-thymidine was omitted from the SIS, then dCTP, dGTP, dTTP, and/or dUTP may also be added.

It is preferred that the complete elongation of the first primering sequence synthesize or polymerize the sequences or information encoded in the single-stranded template, including the first SIS, the fragmented DNA, the second SIS, first primering sequence-binding sequence, and the second primering sequence-binding sequence. It is preferred that the complete elongation of the single-stranded template synthesize or polymerize the sequences or information encoded in the first primering sequence, including the 5' overhang which preferably includes the first index sequence and the first immobilizing sequence.

In some embodiments, therefore, helicase is excluded from the reaction mixture or is inhibited so that random short sequences of oligonucleotides cannot prime DNA polymerase at a position that would result in incomplete replication of the template strand. In some embodiments, therefore, not only is helicase excluded or inhibited, but the DNA polymerase will include an exonuclease activity which will destroy any downstream and therefore incomplete newly synthesized strands when the newly synthesized DNA strand that will become full length is being synthesized.

The time for complete elongation is not particularly limited and may include incubation times from 10 seconds to 10 minutes. It is generally preferred and understood that a time of around 1 minute will suffice to elongate a 1000 to 2000 base pair nucleotide at 72° C. In this regard, the time of the incubation for complete elongation is dependent on the temperatures. For example, a complete elongation incubation at 48° C. may require more time, around 5 minutes to elongate a sequence of 1000 to 2000 base-pairs, whereas the same sequence could be elongated at 72° C. in 1 minute. If the sequence which can be elongated within 1 minute at 72° C. is instead incubated for 5 minutes, the result is still the same because the new strand of DNA will have been completely synthesized and will replicate the full length of the single-stranded DNA acting as a template within that first minute and the double-stranded product will just remain in solution for the remaining 4 minutes of elongation incubation unless the double-stranded product is denatured.

In this regard, it is preferred that if the blocking oligonucleotide is being used and is annealed to the blocking oligonucleotide-binding sequence on the 5' end of the single-stranded template, that the blocking oligonucleotide be removed in order to complete the elongation. One means of removing the blocking oligonucleotide is to denature it by increasing the temperature of the incubation for complete elongation to near or above the melting temperature of the blocking oligonucleotide. For example, if the blocking oligonucleotide has an annealing/melting temperature of 58° C., then increasing the temperature of the incubation for complete elongation to 58° C. will remove 50% of the blocking oligonucleotide annealed to the single-stranded template. On the other hand, increasing the temperature of the incubation for complete elongation to 63° C. will remove more than the 50% of the blocking oligonucleotide annealed to the single-stranded template. Increasing the temperature to 70° C. would remove even more of the blocking oligonucleotide annealed to the single-stranded template than that removed at 63° C. It is generally understood that at around 72° C. nearly 100% of a short nucleotide no greater than 50 base pairs, such as a blocking oligonucleotide, will be removed from the strand to which it is annealed. In this regard, the complete elongation incubation temperature of 72° C. is preferred.

Noted above, the complete elongation incubation time is in part dependent on the temperature. The complete elongation incubation time is also in part dependent on the amount of time the blocking oligonucleotide has been removed from the single-stranded template. Thus, it is preferred to add the omitted dNTP, and increase the temperature to 72° C. However, DNA polymerase just requires two reactants to effectuate complete elongation, the two reactants being 1) all the dNTPs necessary for complete elongation, including the omitted dNTP from the partial elongation reaction mixture and 2) a single-stranded DNA to act as a template, including a single-stranded template from which the blocking oligonucleotide has been removed. Therefore, the order is not particularly limited of admixing the omitted dNTP and the attaining a single-stranded template from which the blocking oligonucleotide has been removed. For example, the omitted dNTP may be added first then the blocking oligonucleotide may be removed by increasing the temperature of the incubation for complete elongation to 72° C. Alternatively, the blocking oligonucleotide may be removed by increasing the temperature of the incubation for complete elongation to 72° C. and then the omitted dNTP may be added. Alternatively still, both the omitted dNTP may be added at the same time as the blocking oligonucleotide is removed by increasing the temperature of the incubation for complete elongation to 72° C. Thus the incubation for complete elongation may comprise, in no particular order, admixing the omitted dNTP and removing the blocking oligonucleotide from the single-stranded template.

Denaturing the Product of the First Primering Sequence/Single-Stranded Template Elongation Thereafter, the product of the elongation of the first primering sequence and/or single-stranded-template should be denatured or deannealed. FIG. 2 illustrates in step "3.1" denaturing of the double-stranded product of the elongation of the first primering sequence and/or the elongation of the single-stranded template. Denaturing may include but is not limited to increasing the temperature of the admixture to preferably near the annealing temperature of the product of the elongation of the first-primer and/or single-stranded-template or more preferably above the annealing temperature of the product of the elongation of the first-primer and/or single-stranded-template, or more preferably still 5° C. above the annealing temperature of the product of the elongation of the first-primer and/or single-stranded-template. It is generally understood that the annealing temperature of a double-stranded DNA can be calculated from known references and computer programs which are largely based off of the work of Ignacio Tinoco Jr, Kenneth Sauer, and/or James C Wang which was published in several manuscripts and books, including IGNATIO TINOCO JR. KENNETH SAUER, AND JAMES C. WANG PHYSICAL CHEMISTRY: PRINCIPLES AND APPLICATIONS IN BIOLOGICAL SCIENCES 165-167 ($3^{rd}$ ed. 1995), which is hereby incorporated by reference. See also Breslauer et al. 83 PROC. NATL. ACAD. SCI. 3746, also hereby incorporated by reference. In this regard, the melting/annealing temperature of the double-stranded DNA is calculated by determining the Gibbs free energy of the double-stranded DNA and then calculating the temperature at which 50% of the DNA will be in a double-stranded form and 50% will be in a single-stranded form. Several examples are provided above regarding how the melting temperature of a double-stranded DNA can vary with length and relative G/C content. The same principles apply to the product of the elongation of the first-primer and/or single-stranded-template. However, because the double-stranded product of the elongation of the first-primer and/or single-stranded-template includes the fragmented DNA, whose sequence is unknown, it is generally preferred to increase the temperature of the product of the elongation of the first-primer and/or single-stranded-template to a temperature from 95° C. to 100° C. In general, all double-stranded DNA will have an annealing/melting temperature less than 95° C. under physiological and/or typical in vitro conditions used for molecular biology. Therefore, in general DNA of all lengths and all relative guanine/cytosine to adenine/thymidine content will be completely melted or denatured from 95° C. to 100° C.

Annealing Second Primering Sequence

In preferred embodiments, the second primering sequence may anneal to the second primering sequence-binding sequence (b3) and possibly the first primering sequence-binding sequence (b1) on the 3' end of the single-stranded template. FIG. 2 illustrates in step "3.1" annealing of the second primering sequence (labeled for illustrative purposes only the "PS-2") to the product of the elongation of the first primering sequence and/or the elongation of the single-stranded template (in this regard, the step illustrates only the annealing of the second primering sequence to the elongated first-primer, but the annealing of the second primering sequence to the elongated single-stranded template is also contemplated). The second primering sequence is not particularly limited so long as it anneals to the 3' end of the single-stranded template and it has a free 3'-OH permitting elongation. The second primering sequence may have a sequence which is partially complementary to the blocking-oligonucleotide binding sequence, or more preferably, the second primering sequence may have a sequence that is fully complementary to the second primering sequence-binding sequence. In FIGS. 1 and 4, the sequence "b3" illustrates the sequence in which the second primering sequence-binding sequence of the adaptors may be located. The second primering sequence may have an additional sequence which binds to the sequence of the adaptor sequence outside of the second primering sequence-binding sequence, including for example, the first primering sequence-binding sequence. For example, FIG. 4 shows the second primering sequence (PS-2) annealing to region b1 (the first primering sequence-binding sequence), b2 (the first incidence in the 3' to 5' direction of the nucleotide omitted from the strand identifier sequence and the first primering sequence-binding sequence), and all of the second primering sequence-binding sequence, b3. FIG. 4 also shows the second primering sequence having high homology to b1, b2 and b3.

The Components of the Second Primering Sequence

In preferred embodiments, the second primering sequence may comprise additional sequences in a 5' direction from the sequence which binds to the second primering sequence-binding sequence. Thus, when annealed to the second primering sequence-binding sequence, the second primering sequence will comprise sequences that "over-hang" the 3' end of the product of the elongation of the first-primer and/or single-stranded-template. For convenience, these additional sequences in a 5' direction from the sequence of the first primering sequence which binds to the blocking oligonucleotide-binding sequence will be known as the "5' overhang sequence of the second primering sequence." This overhang sequence may comprise a second index sequence, a second sequencing sequence and/or a second immobilizing sequence. The properties of the second index sequence are the same as that of the first index sequence and are described above. The sequence of nucleotides in the second index sequence may be different or the same as the sequence of nucleotide in the first-index sequence.

The Second Primering Sequence May Comprise a (Second) Immobilizing Sequence and (Second) Sequencing Sequence The second immobilizing sequence may be designed with a sequence that anneals to a second immobilizer sequence. As described further, the second immobilizer sequence will be bound at the 5' end to a solid-state support. Hence, when the second immobilizer sequence anneals to the second immobilizing sequence, a DNA strand comprising the second immobilizing sequence will be immobilized by the second immobilizer sequence bound to the solid-state support.

The second sequencing sequence, if included in the second primering sequence, may anneal to a second sequencing primer. In certain embodiments, the second sequencing primer is a primer that initiates the elongation of the fragmented DNA during sequencing by synthesis. Once the second sequencing primer is annealed and is being elongated during sequencing-by-synthesis, the machine performing the sequencing by synthesis will detect the incorporation of each nucleotide into the newly synthesized strand of DNA, thus sequencing the template strand of fragmented DNA by the order in which nucleotides are newly incorporated into the daughter strand of DNA. The second sequencing sequence may omit the nucleotide omitted from the SIS and/or the primering sequence-binding sequence. If omitted, the second sequencing primer which anneals to the second sequencing sequence may in turn omit the nucleotide which base-pairs to the nucleotide omitted from the second sequencing sequence.

When the second primering sequence comprises a sequence which anneals to the second primering sequence-binding sequence, a second index sequence, and a second immobilizing sequence, it is preferred that the order of the sequences be as followed from 3' to 5': the second primering sequence-binding sequence, the second index sequence, and the second immobilizing sequence.

The second primering sequence may contain sequences and chemical modifications, including but not limited to those that will facilitate the use for multiple downstream sequencing approaches. For example, the second primering sequence may contain restriction sites or homing endonuclease sites to facilitate the downstream addition of custom adaptors at both ends, including Y shaped DNA adaptors, or DNA hairpins. The second primering sequence may contain sequence to facilitate the attachment to a solid matrix such as a surface (eg. flow-cell) or a bead. The sequences present in second primering sequence might allow the use of bridge amplification by the presence of complementary oligonucleotides attached to a surface. The sequences present in second primering sequence might also allow the use of water in oil based emulsion PCR amplification and attachment to beads. The second primering sequence may contain sequences allowing for the formation of DNA concatemers to facilitate the sequencing of long stretched of DNA. The second primering sequence may contain sequences such as hairpin loops allowing for the formation of covalently closed DNA molecule to facilitate the sequencing of concatemers of copies of sense and antisense strands. The sequences present in the second primering sequence might facilitate the targeting to exonucleases used in exonuclease sequencing. The sequences present in the second primering sequence might facilitate targeting to nanopores used in nanopore sequencing. The sequences present in the second primering sequence might facilitate targeting to DNA or RNA polymerases, helicases, ribosomes, RNA binding proteins or transcription factors. The second primering sequence may also comprise modifications such as biotin, digoxigenin, thyol modified nucleotides, cholesterol, surfactants, click-chemistry or any other reactive group that facilitates their binding to a solid or a lipid membrane support with complementary chemistry.

The second primering sequence is not limited to binding to the elongated first-primer or the elongated single-stranded template because the primary purpose of annealing the second primering sequence is to conserve the genetic information that is in the elongated first-primer or the elongated single-stranded template while also introducing into the conserved genetic sequence the information encoded in the 5' overhang of the second primering sequence, including optionally the second index sequence and the second immobilizing sequence. The elongated first primering sequence has encoded in it the genetic sequence of the single-stranded template (but in complementary form). The elongated single-stranded template has encoded in it the genetic sequence of the first-primer, including the first-index sequence and the first immobilizing sequence (but in complementary form). Thus, the second primering sequence may bind to either the elongated single-stranded template or the elongated first primering sequence or to both the elongated single-stranded template and the elongated first primering sequence. In this regard, however, it is less preferred that the flow cell have bound to it the second primering sequence in both complementary forms. Therefore, it is less preferred to have the second primering sequence-binding to both the elongated single-stranded template and the elongated first primering sequence. The binding to both the single-stranded template and the elongated first primering sequence would result in two products being produced in the next elongation step, but only one of those two products would be worthwhile immobilizing to the flow cell with the second sequence.

[It is preferred that the final concentration of second primering sequence in the admixture of second primering sequence and the product of the elongation of the first primering sequence and/or single-stranded-template be from 1 nM to 20 µM, more preferably from 100 nM to 5 µM, more preferably still from 500 nM to 2 µM, and more preferably still 1 µM. It is preferred that the concentration of second primering sequence to the admixture of second primering sequence and other components of the admixture be from 1 nM to 20 µM, more preferably from 100 nM to 5 µM, more preferably still from 500 nM to 2 µM, and more preferably still 1 µM.

In some embodiments, it is preferred that the second primering sequence have an annealing temperature higher than the temperature at which the first primering sequence and blocking oligonucleotide anneal. A discussion of the conditions allowing for the design of the second primering sequence, such that it may have an annealing/melting temperature higher than that of the first primering sequence and blocking oligonucleotide can be found above. In this regard, the conditions for designing the second primering sequence to have a higher melting temperature are similar to the conditions for designing the first primering sequence and blocking oligonucleotide. It is noted above that one condition can increase the melting/annealing temperature of an oligonucleotide is increasing the length of the primer and/or increasing the relative G/C content. In this regard, the second primering sequence can be designed to have a higher melting/annealing temperature than that of the first primering sequence and blocking oligonucleotide by increasing the length of the second primering sequence relative to the first primering sequence and/or blocking oligonucleotide that is the second primering sequence can be designed not only to bind to the second primering sequence-binding sequence but also the first primering sequence-binding sequence. FIG. 4 also shows the second primering sequence having high homology to b1, b2 and b3.

In some embodiments, it is preferred that the second primering sequence have an annealing/melting temperature to the product of the elongation of the first-primer and/or single-stranded-template equal to or greater than 62° C. In some embodiments, it is preferred that the second primering sequence have an annealing temperature to the product of the elongation of the first-primer and/or single-stranded-template from 62° C. to 66° C. In some embodiments, it is preferred that the second primering sequence have an annealing temperature at 64° C. In some embodiments, where the first primering sequence and optionally the blocking oligonucleotide have annealing temperatures to the single-stranded template below 50° C., it is preferred that the second primering sequence have an annealing temperature to the product of the elongation of the first-primer and/or single-stranded-template from 55° C. to 65° C. In such embodiments, it is further preferred that the second primering sequence have an annealing temperatures from 58 to 62° C.

In some embodiments, the actual temperature setting for the annealing of the second primering sequence may be lower than the annealing temperature of the second primering sequence. That is, the annealing temperature of the second primering sequence, as defined above, is the temperature at which 50% of the second primering sequence is bound to the product of the elongation of the first-primer and/or single-stranded-template and is determined by the Gibb's Free Energy of the association between the two strands. In order to have more than 50% binding of the second primering sequence, it is preferable that the actual temperature of the product of the elongation of the first-primer and/or single-stranded-template and second primering sequence admixture be lower than the annealing temperature of the second primering sequence (this is referred to as the actual temperature of annealing of the second primering sequence). For example, the actual temperature of annealing may be 5° C. than the annealing temperature of the second primering sequence.

However, it is not preferred that the blocking oligonucleotide compete for binding of the blocking oligonucleotide to the product of the elongation of the first-primer and/or single-stranded-template. Therefore it is not preferred that the actual temperature of annealing of the second primering sequence be within the range at which at least 10% of the blocking oligonucleotide would bind to the product of the elongation of the first-primer and/or single-stranded-template. It is even more preferred that the actual temperature of annealing of the second primering sequence be within the range at which at least 1% of the blocking oligonucleotide would bind to the product of the elongation of the first-primer and/or single-stranded-template. It is even more preferred that the actual temperature of annealing of the second primering sequence be within the range at which at least 0.1% of the blocking oligonucleotide would bind to the product of the elongation of the first-primer and/or single-stranded-template. It is even more preferred that the actual temperature of annealing of the second primering sequence be within the range at which at least none of the blocking oligonucleotide would bind to the product of the elongation of the first-primer and/or single-stranded-template. Thus, it is preferred that if the annealing temperature of the blocking oligonucleotide is 58° C. or less, that the actual temperature of annealing of the second primering sequence be at least 60° C. It is preferred that the actual temperature of the annealing of the second primering sequence be at least 5° C. higher than the annealing temperature of the blocking oligonucleotide. It is further preferred that the actual temperature of the annealing of the second primering sequence be at least 7° C. higher than the annealing temperature of the blocking oligonucleotide. It is further preferred that the actual temperature of the annealing of the second primering sequence be at least 10° C. higher than the annealing temperature of the blocking oligonucleotide.

In some embodiments, it is preferred that 95% of the product of the elongation of the single-stranded template and/or first primering sequence be annealed to a second primering sequence at 60° C. In some embodiments, it is preferred that 99% of the product of the elongation of the single-stranded template and/or first primering sequence be annealed to a second primering sequence at 60° C. In some embodiments, it is preferred that 99.9% of the product of the elongation of the single-stranded template and/or first primering sequence be annealed to a second primering sequence at 60° C. In some embodiments, it is preferred that 99.99% of the product of the elongation of the single-stranded template and/or first primering sequence be annealed to a second primering sequence at 60° C. In some embodiments, it is preferred that 99.999% of the product of the elongation of the single-stranded template and/or first primering sequence be annealed to a second primering sequence at 60° C. In some embodiments, it is preferred that all of the product of the elongation of the single-stranded template and/or first primering sequence be annealed to a second primering sequence at 60° C.

If the second primering sequence binds to the elongated first primering sequence, and if the elongated first primering sequence has a second primering sequence-binding sequence of "b3 prime" because the second primering sequence-binding sequence of the elongated first primering sequence used the single-stranded template as a template to encode it, then the sequence of the second primering sequence which anneals to at least the second primering sequence-binding sequence of the elongated first primering sequence will have a sequence of "b3." In such an embodiment, the blocking oligonucleotide may also have a sequence which binds to the elongated first primering sequence of "b3." In both embodiments where the second primering sequence has a sequence of b3 and b3 prime, it is still preferable that the second immobilizing sequence still be identical (that is non-complementary).

In some embodiments, the second and first primering sequence annealing steps may undergo several cycles, as in polymerase-chain reactions, to form the final product. In this regard, after a product of the elongation of the first-primer and/or single-stranded template has been attained, the second primering sequence may anneal to the product of the elongation of the first primering sequence and/or single-stranded template. Thereafter, the second primering sequence will be annealed and once another cycle is initiated, the first primering sequence may bind to the elongated second primering sequence, or the second primering sequence may bind to the elongated product of the first-primer and/or single-stranded template. FIG. 7 illustrates how the products will be amplified through multiple rounds of polymerase chain reactions of annealing the first and second primering sequences to either the single-stranded template or any subsequent reaction products.

While the second primering sequence anneals to the product of the elongation of the single-stranded template and/or first primering sequence, the second primering sequence may be admixed earlier to the composition. The timing of the admixture of the second primering sequence in part depends upon whether a blocking oligonucleotide, which is optional, is utilized. For example, if the blocking oligonucleotide is utilized, then the second primering sequence may be admixed when the omitted dNTP is admixed but after the blocking oligonucleotide is admixed. The blocking oligonucleotide would thus prevent the binding of the second primering sequence until at least after the elongation of the first primering sequence and/or the elongation of the single-stranded template. Alternatively, the second primering sequence may be admixed after the dNTP is admixed, after removal of the blocking oligonucleotide from the single-stranded template, or after the elongation of the first primering sequence and or the elongation of the single-stranded template. In this regard, the second primering sequence may be admixed before or after the denaturation of the product of the elongation of the single-stranded template and/or first primering sequence. However, if the second primering sequence is admixed after the denaturation of the product of the elongation of the single-stranded template and/or first primering sequence, and if the temperature of the product of the elongation of the single-stranded template and/or first primering sequence lowers before the admixture, thus creating a double-stranded product again, then it may be worthwhile to denature the admixture containing the second primering sequence again before lowering the admixture to the actual temperature of annealing the second primering sequence.

Likewise it is possible to use RNA polymerase, and an RNA polymerase promoter near the 5' end of the elongated first primering sequence to perform in vitro translation which may provide multiple copies of the elongated first primering sequence. FIG. 8 illustrates an embodiment generating an RNA sequence incorporating the first-primer and the single-stranded template then annealing a second primering sequence and reverse transcribing the RNA sequence to generate a cDNA comprising the second primering sequence, the fragmented DNA, and the first primering sequence. Then the second primering sequence could be annealed to the RNA copy of the elongated first primering sequence and the second primering sequence could be elongated by reverse transcriptase to make a cDNA copy of the RNA copy of the elongated first primering sequence which now incorporates the second primering sequence including the 5' overhang of the second primering sequence. The cDNA could then be amplified by PCR using the first primering sequence and the second primering sequence or alternatively, it could incorporate a modified first primering sequence or second primering sequence which have additional 5' overhang sequences.

Elongation of the Second Primering Sequence and/or the Product to Which it is Annealed After the second primering sequence has annealed to the above mentioned product, the temperature of the admixture may be increased to increase the efficiency of the elongation of the admixture. FIG. 2 illustrates in step "3.2" elongation of the second primering sequence (labeled for illustrative purposes only the "PS-2") and the elongation of the product of the elongation of the first primering sequence and/or the elongation of the single-stranded template. To facilitate elongation, additional reagents for the elongation, including dNTPs, DNA polymerase, etc. may be added, or the elongation may rely on the reagents added earlier, such as during the partial and/or complete elongation of the single-stranded template and/or first primering sequence. As the conditions may already be set for elongation, the elongation may proceed entirely at the actual temperature of annealing of the second primering sequence. Or, after a short extension which would increase the melting temperature of the extended second primering sequence and the above mentioned product, the temperature may be increased to increase the efficiency and speed at which the DNA polymerase will complete the elongation. For example, the temperature may be set at 62° C. for 10 seconds to 30 seconds, allowing for annealing of the second primering sequence and some extension of the second primering sequence and above mentioned product, and then the temperature may be increased to 72° C. or any temperature below the melting temperature of the product of this second elongation step. The preferred temperature for elongation may be anywhere from 62° C. to 72° C., and the preferred time to complete the elongation may be anywhere from 1 minute to 10 minutes.

The time for complete elongation is not particularly limited and may include incubation times from 10 seconds to 10 minutes. It is generally preferred and understood that a time of around 1 minute will suffice to elongate a 1000 to 2000 base pair nucleotide at 72° C. In this regard, the time of the incubation for complete elongation is dependent on the temperatures. For example, a complete elongation incubation at 48° C. may require more time, around 5 minutes to elongate a sequence of 1000 to 2000 base-pairs, whereas the same sequence could be elongated at 72° C. in 1 minute. If the sequence which can be elongated within 1 minute at 72° C. is instead incubated for 5 minutes, the result is still the same because the new strand of DNA will have been completely synthesized and will replicate the full length of the single-stranded DNA acting as a template within that first minute and the double-stranded product will just remain in solution for the remaining 4 minutes of elongation incubation unless the double-stranded product is denatured.

Subsequent PCR and/or Bridge-Amplification to Create Clusters

For samples with low amounts of DNA, the amount of fragmented DNA and therefore the amount of DNA comprising the fragmented DNA, the adaptor sequences, and the first and second primering sequences may not be sufficient to undergo bridge-amplification to create clusters prior to sequencing. In such an event, it may be worthwhile performing a PCR amplification using the same sequences as the first and second immobilizer sequences, but wherein such primers are not coupled to solid state support (i.e. they are free floating and are thus able to be amplified by traditional PCR in solution without solid state support). Such primers which are not coupled to solid state support are not particularly limited so long as they comprise a 3'-OH end which will permit elongation of the primer.

Likewise the first and second immobilizer sequences are not particularly limited as long as they comprise a free 3'-OH end available for primer elongation. The first and second immobilizer sequences may be grafted onto the surface of a solid state support. In preferred embodiments, the first and second immobilizer sequences may be cleavable from the solid state support via, for example, a nickase. The first and second immobilizer sequences are preferably at least 5 bp long, preferably less than 100 bp long, more preferably still less than 50 bp long. The first and second immobilizer sequences may have two different sequences bound to the surface of the flow cell, (also known as flow cell oligomers or flow cell sequences).

In some embodiments, the 5' overhang of the annealed and elongated primering sequences can have the functional property of annealing or binding to the flow cell oligomers or flow cell sequences. When the 5' overhang of the annealed and elongated primering sequences bind to the flow cell oligomers or flow cell sequences, they are known as flow-cell recognition sequences. As noted, the flow cell could have two "different" oligomers—the oligomers are different with regard to the dissimilarities of the sequences of base-pairs in the oligomers. The differences are also functional, in that the sequences are so dissimilar that a flow-cell recognition sequence would bind to only one of the two flow cell oligomers. A flow-cell with two different oligomers bound to it will have one, several, tens, hundreds, thousands, tens of thousands, hundreds of thousands, millions, tens of millions, hundreds of millions, billions, tens of billions, $10^7$, $10^8$, $10^9$, $10^{10}$, $10^{11}$, $10^{12}$, $10^{13}$, etc. of each of the two different flow cells oligomers bound to the surface. The flow cell oligomers (also known as a first immobilizing primer and second immobilizing primer as in U.S. Pat. No. 7,985,565) will be bound to the flow cell at their 5' end. Each of the two types of flow cell oligomers will be "clustered" or within "colonies" (as in U.S. Pat. No. 7,985,565) with about several hundred to several thousand of each of the two types of flow cell oligomers within each cluster or colony. Each cluster or colony will be segregated from the next cluster or colony by a space of about 1 to 5 width of each cluster or colony. Each colony or cluster will measure 10 nm to 100 μm across their longest dimension, more preferably from 100 nm to 10 μm across their largest dimension. Colonies or clusters may be provided at a density of over one colony/mm² of flow cell surface area (solid state support) and more preferably the density of colonies may be over $10^2$, $10^3$, $10^4$ colonies or clusters per mm² of flow cell surface area (solid state support). More preferably still, the density of colonies may be over 105 and 106 colonies or clusters per mm² of flow cell surface area (solid state support).

Each cluster or colony will comprise the first and second immobilizer sequences. The density of the first and second immobilizer sequences will be such that the distance between most if not all of the first immobilizer sequences and most if not all of the second immobilizer sequences will be less than the distance of the fragmented DNA comprising the adaptors, and first and second primering sequences. This way the first immobilizing sequence at the end of the fragmented DNA will anneal to the first immobilizer sequence and the second immobilizing sequence will be sufficiently close that it may anneal with the second immobilizer sequence at the other end of the fragmented DNA. Preferably there will be substantially equal proportions of first and second immobilizing sequences within a colony.

The bridge-amplification process of U.S. Pat. No. 7,985,565 will then be carried out wherein the fragmented DNA comprising the adaptor sequences, the first primering sequences, and the second primering sequences will be annealed to either the first and/or second immobilizer sequences. The 3'-OH of the first and/or second immobilizer sequences will then be elongated, using the fragmented DNA comprising the adaptor sequences, the first primering sequence, and the second primering sequence, as a template—the genetic information within the fragmented DNA comprising the adaptor sequences, the first primering sequence, and the second primering sequence will thus be transferred to the first or second immobilizer sequences and thus bound to the solid state support. The fragmented DNA comprising the adaptor sequences, the first primering sequences, and the second primering sequences will then be denatured or deannealed and removed. The bound fragmented DNA will then be annealed to the immobilizer sequence at the free end of the bound fragmented DNA.

For example, if the fragmented DNA is bound to the first immobilizer sequence then the free end of the fragmented DNA will have the second immobilizing sequence bound and the second immobilizing sequence will anneal to the second immobilizer sequence. The 3'-OH of the newly bound immobilizer sequence (for example, in the above illustration the second immobilizer sequence) will be elongated to comprise the fragmented DNA, the adaptor sequences, and the first and second primering sequence. These double-stranded products will then be denatured or deannealed and then the free ends, either the first or second immobilizing sequences, will anneal to their respective first and second immobilizer sequences and be elongated again. This process will be repeated until cluster generation is completed. The repetition of this process may involve a 1000 fold amplification of the fragmented DNA sequence originally bound within the cluster so that all or substantially all of the first and second immobilizer sequences are bound.

Next the double-stranded immobilized molecules present in a colony are cleaved and this is followed by a denaturing step. Alternatively a denaturing step could be used initially and could be followed by a cleavage step. Cleavage may be made enzymatically. However other means of cleavage are possible, such as chemical cleavage. Denaturing can be performed by any suitable means described above. For example, it may be performed by heating, use of helicase, and/or by changing strength of the hydrogen bonding forming the base-pairing by changing the pH or ionic strength of the medium. In this regard, it is generally preferred that only one of the two strands be cleaved. For example, the strand bound to the second immobilizer sequence may be cleaved from the second immobilizer sequence. Alternatively, the strand bound to the first immobilizer sequence may be cleaved from the first immobilizer sequence. As these sequences were replicated by elongation, the cleavage should break the sugar-base backbone of the nucleotide sequence. It is preferred that the cleavage leave the first or second immobilizer sequence bound to the surface of the solid state support.

A restriction endonuclease cleavage site may be located within the first or second immobilizer sequence. A first or second immobilizer sequence may also be provided with a restriction endonuclease recognition site for a Type II restriction endonuclease which directs DNA cleavage outside of the first or second immobilizer sequences. Alternatively a cleavage site and/or a recognition site may be produced within the adaptor sequences, the first primering sequence-binding sequence, or the blocking oligonucleotide binding sequence. In any event, restriction endonucleases can be useful in allowing only one of the two complementary strands of fragmented DNA (i.e. one being sense the other being antisense, or alternatively one being forward and the other being backward) within a colony to be cleaved so as to leave free a part of the released immobilizer sequence which is sufficient to permit a reannealing of the immobilizing sequence at the free end of the other strand of fragmented DNA. At this point in time, the cluster generation process has been completed and the flow cell is configured in such a way as to permit sequencing by synthesis by the reannealing of the free immobilizing sequence to the cleaved and therefore free immobilizer sequence. After priming, each nucleotide may be incorporated into the newly synthesized strand of DNA based on the template strand annealed to the solid state support during cluster generation. Each nucleotide being incorporated into the newly synthesized strand is associated with a different fluorophore, and each fluorophore may emit a different wave-length of light when the newly incorporated nucleotide may be integrated into the new strand of DNA and/or base-pairs with its complementary counterpart (A to T, G to C) during elongation. The first or second primering sequence may contain sequences or modifications to facilitate the attachment of the nucleic acid molecule to a lipid membrane or bilayer. Typical modifications to attach a sequence to a lipid membrane include, but are not limited to, thiol, biotine, cholesterol, tocopherol or surfactants (e.g., lipids, palmitate . . . ). The first or second primering sequence may contain sequences complementary to a nucleotide attached to a lipid bilayer. The primering sequence may contain also elements to facilitate the interaction with DNA or RNA polymerases, helicases, ribosomes, transmembrane pores or exonucleases such as the ones used in stochastic or single molecule nucleic acid sequencing approaches.

In exonuclease based nanopore sequencing the nucleic acid may be digested and the produced free nucleotides will be identified by their effect on the electric potential across a lipid a membrane. A single stranded nucleic acid strand might also be forced to pass through a nanopore driven by differences in the electric potential or assisted by enzymes such helicases or a polymerases. The movement of the nucleic acid strand through the nanopore may produce a change in electric potential allowing the identification of the nucleic acid sequence. The primering sequence may contain sequences to facilitate the attachment of a nucleic acid sequence forming a hairpin loop, which will allows the covalent linkage of the two strands in a double stranded nucleic acid template. The presence of a hairpin loop attached to the primering sequence will allow to link covalently both strands of the nucleic acid template and delineate (divide) both strands in the double stranded nucleic acid template. This will allow sequencing consecutively both strands of a double stranded nucleic acid molecule that will be delimited by the sequence of the sequence of the hairpin loop. Sequencing both strands of the same molecule will increase the sequencing quality. A hairpin loop can be also present at both sides of a template generating a closed circular nucleic acid molecule formed by an internal double stranded nucleic acid template delimited by two hairpin loops (dumbbell shape). That would allow multiple consecutive cycles sequencing the template, hairpin loop 1, reverse complement to the template and hairpin 2. The generation of this closed nucleic acid dumbbell molecule will allow the amplification of the molecule by a DNA or RNA polymerase with strand displacement or 5'-3'exonuclease activity. This is the case in molecular biology techniques such as rolling circle amplification using the Phi29 DNA polymerase, or DNA sequencing of concatemers of copies of sense and antisense strands as in U.S. Pat. No. 9,910,956, which incorporated by reference. Sequencing of concatemer copies of the sense and antisense strand of the same molecule will allow to increase sequencing quality by generating a circular consensus molecule of the original nucleic acid insert. A DNA or RNA polymerase immobilized in a surface may incorporate fluorescent-labeled nucleotides using as template a closed circular nucleic acid molecule with hairpin loops at both ends (dumbbell). By limiting the illumination to a small region surrounding where the DNA or RNA polymerase is immobilized, individual fluorescent labeled nucleotide incorporation events may be detected at single molecule resolution.

The index sequence may then be used to identify the samples of the sequences, and the SISs may be used during strand alignment and single-strand consensus sequence alignment and duplex consensus sequence alignment to distinguish true mutants from misinsertions caused after the DNA fragmentation.

In some embodiments, during the synthesis/polymerization or elongation of a new strand of DNA from a template strand, (see description of Elongation), DNA polymerase will sometimes incorrectly position a base which does not base-pair with the nucleotide opposite it on the other strand of DNA—this is referred to as a mismatch or misinsertion. In this regard, the newly synthesized strand of DNA may be considered to be complementary to the template strand, even though one or several mismatches may occur. In embodiments, it is contemplated that this mismatching error by DNA polymerase may occur in a daughter strand of DNA, and that the nucleotide sequences comprising SISs incorporated into the genetic information of the daughter molecules may permit tracking of these mismatches and discrimination of these mismatches from genetic polymorphisms (e.g. mutations) found in the genomic DNA as extracted from the cell.

Also embodied are kits and products comprising the adaptors, the first primering sequences, and the second primers and optionally the blocking oligonucleotides. As provided in embodiments above, the adaptors, first primering sequences, and second primering sequences can each be ligated or annealed in separate steps. The kit and products can thus comprise each of the adaptors, first primering sequences, and second primering sequences, and optionally the blocking oligonucleotides individually packaged. Alternatively, the kit and products can comprise, for example, the first primering sequence packaged in a composition or mixture with the blocking oligonucleotide. The kit and products can further comprise a partial elongation or partial polymerization reaction mixture comprising a DNA polymerase and a dNTP mix lacking in at least one of dATP, dGTP, dCTP, dTTP, with the proviso that if dTTP is lacking then dUTP is also lacking.

In embodiments, if a nucleotide sequence is being referred to, it is understood that deoxyribo-adenine monophosphate and adenine (the base-pair) may be used synonymously, likewise deoxyribo-thymidine monophosphate and thymidine (the base-pair) may be used synonymously, deoxyribo-guanine monophosphate and guanine (the base-pair) may be used synonymously, deoxyribo-cytosine monophosphate and cytosine (the base-pair) may be used synonymously, and deoxyribo-uracil monophosphate and uracil (the base-pair) may be used synonymously. Deoxyribonucleotide triphosphates include but are not limited to dATP, dCTP, dGTP, or dTTP. Ribonucleotide triphosphates include but are not limited to rATP, rCTP, rGTP, or rUTP.

In some embodiments, the methods and products require that two nucleotides or two sequences of nucleotides base-pair with one another. Base-pairing may refer to how monophosphate nucleobases orient in a specific and semi-conserved manner due to the ability of bases to form hydrogen bonds with a specific base across from one another in the two strands of oligonucleotides. "Base-pairing" may be used to generally describe the conservation of genetic information during replication not only in vivo but also in vitro such as after isolation and/or fragmentation of the DNA and any post-isolation processes in which nucleic acids anneal and are elongated. Base-pairing may, thus, refer to the interaction between two polynucleotides or oligonucleotides even under conditions where there is not the polymerization of one strand of DNA from another strand of DNA via replication.

In some embodiments, the specificity of base-pairing may be illustrated by example and may include Watson-Crick examples of base-pairing and non-Watson-Crick examples of base-pairing. For example, in Watson-Crick examples of base-pairing, deoxyribo-adenine monophosphate (dAMP, or A), when incorporated into a DNA sequence, may base-pair with deoxyribo-thymine monophosphate (dTMP or T), and vice versa. The adenine-thymine base-pairing may occur because adenine and thymine form two hydrogen bonds across each other when opposite one another on an anti-parallel strand of DNA or possibly RNA. Deoxyribo-cytosine monophosphate (dCMP or C), when incorporated into a DNA sequence, may base pair with deoxyribo-guanine monophosphate (dGMP or G), and vice versa. The cytosine-guanine base-pairing may occur because cytosine and guanine form three hydrogen bonds across each other when opposite one another on an anti-parallel strand of DNA or RNA. Likewise, ribo-cytosine monophosphate (rCMP), when incorporated into a RNA sequence, may base-pair with ribo-guanine monophosphate (rGMP), and vice versa. Ribo-adenine monophosphate (rAMP), when incorporated into a RNA sequence, may base-pair with ribo-uracil monophosphate (rUMP), and vice versa. The adenine-uracil base-pairing may occur because adenine and uracil form two hydrogen bonds across each other when opposite one another on an anti-parallel strand of RNA or possibly DNA.

In non-Watson-Crick examples of base pairing, guanine can orient opposite uracil and adenine can orient opposite adenine to sometimes allow RNAs to fold into three dimensional structure. Non-Watson-Crick base-pairing may comprise wobble-base-pairs which may be incorporated into annealed DNA strands. Wobble base pairs may include 8-oxo-dA and 8-oxo-dG, where the wobble base can pair with a first nucleotide base in a complementary oligonucleotide strand but that when employed within a template strand for elongation, leads to the incorporation of a second nucleotide base different from the predicted-Watson-Crick bases-pairing above, into the newly synthesized strand. Accordingly, the incorporation of a wobble base will result in a mismatch in the newly synthesized strand from the template strand, thus changing the genetic code in any daughter strands synthesized from the newly synthesized strand. A "mismatch" may also refer to when two strands of oligonucleotides fail to undergo Watson-Crick bonding in at least one nucleotide in the sequence during annealing.

In some embodiments, duplex may include the double-stranded binding product of DNA, RNA, or the combination of both RNA and DNA, whereby at least two oligonucleotides anneal. In some embodiments, annealing may include the process whereby the at least two oligonucleotides undergo sufficient Watson-Crick-type and non-Watson-Crick-type base-pairing so that a stable duplex is formed at a particular temperature even if at least one or several nucleotides or one or several stretches of nucleotides do not undergo Watson-Crick-type and non-Watson-Crick-type base-pairing with a corresponding opposite nucleotide, nucleotides, or stretches of nucleotides on the other strand of oligonucleotide. In some embodiments, full complementarity or fully complementary may include the relationship between two oligonucleotides in a duplex whereby all of the nucleotides on one strand form Watson-Crick base-pairs with the nucleotides on the other strand in the entirety of the sequence. In some embodiments, partial complementarity or partially complementary may include the relationship between two oligonucleotides in a duplex whereby at least a sufficient number of nucleotides on one strand form Watson-Crick base-pairs and non-Watson-Crick base-pairs with nucleotides on the other strand in order to anneal and form a stable duplex at a given temperature despite the failure of a number of nucleotides in one oligonucleotide to form base-pairs with the nucleotide opposite them in the other oligonucleotide to contribute to the strength of the bonding between the two strands of oligonucleotides in the duplex. In this regard, complementarity and complementary may include full and partial complementarity and fully and partially complementary respectively.

EXAMPLES

The following provides non-limiting examples of an adapter sequence comprising SIS. As noted above, the SIS may have a varying sequence, which may be one of any four or three nucleotides. Accordingly, each nucleotide in the variable SIS sequence is labeled as "N".

```
Example adapter 1:
Long oligo containing (b1, b2, b3, SIS and A, in
5'-3' direction):
                                            (SEQ ID NO: 1)
5'OH-GACTGGAGTTCAGACGTGAGCTCTTCCGTTCTNNNNNNGCCAAT
GC*T-3'OH Short oligo (A'):
5'Phos-GCATTGGC-3'OH Example adapter 2:
Long oligo containing (b1, b2, b3, SIS and A, in
5'-3' direction):
                                            (SEQ ID NO: 2)
5'OH-GACTGGAGTTCAGACGTGAGCTCTTCCGTTCTNNNNNNTCACTG
CG*T-3'OH
```

```
-continued
Short oligo (A'):
5'Phos-CGCAGTGA-3'OH

Examples of the First Primering Sequence.
Examples of Index sequence (IS-1) in bold,
* identifies a phosphorothioate bound.

(SEQ ID NO: 3)
5'OH-AATGATACGGCGACCACCGAGATCTACACAGGCGAAGACACTCT
TTCCCTACACGACGCTCTTCCGTTC*T-3'OH (SEQ ID NO: 4)
5'OH- AATGATACGGCGACCACCGAGATCTACACTAATCTTAACACTC
TTTCCCTACACGACGCTCTTCCGTTC*T-3'OH

Examples of the Second Primering Sequence.
Examples of Index sequence (IS-2) in bold, "*"
represents a phosphorothioate bound.

(SEQ ID NO: 5)
5'OH-CAAGCAGAAGACGGCATACGAGATTAATGCGCGTGACTGGAGTT
CAGACGTGTGCTCTTCCGATC*T-3'OH (SEQ ID NO: 6)
5'OH-CAAGCAGAAGACGGCATACGAGATCGGCTATGGTGACTGGAGTT
CAGACGTGTGCTCTTCCGATC*T-3'OH

Example of blocking oligonucleotide. "/InvdT/"
Represents an inverted dT to block 5'-3'elongation
of the blocking oligo.

(SEQ ID NO: 7)
5'OH-CGGAAGAGCTCACGTCTG/InvdT/-3'OH
```

Experimental Results

Experiments have been conducted using the protocol from Sophia Genetics Solid Tumour Solution (STS) for all steps except the adapter annealing and pre-capture PCR (https://www.sophiagenetics.com/fileadmin/documents/pdf/Article/STSbySG_FS.pdf). This protocol applies conventional fragmentation of genomic DNA, end repair and annealing, bead purification, capture, and post-capture PCR. In the experiments to demonstrate the applicability of the proposed methods, for adapter annealing, the adapter sequences of the above examples 1 and 2, comprising SIS, have been used. For PCR, dedicated steps have been applied as follows.

Adapter annealing: Adapters must first be annealed in any suitable annealing buffer. For the experiments, 50 mM Tris-HCl pH 8 with 62.5 mM NaCl. was used. The short and long oligos of each adapter were mixed at 15 μM each in annealing buffer, for instance 15 μl of the adapter example 1 long oligo with 15 μl of the adapter example 1 short oligo in 70 μl of annealing buffer. Each adapter was then run through the following program in the thermocycler:
95° C.-5 min
slow cool to 65° C.
65° C.-1 min
slow cool to 37° C.
37° C.-1 min
slow cool to 10° C.

The resulting solution was always kept on ice or frozen. The adapters were then mixed in equal amounts to make the final 15 μM adapter mix.

Adapter ligation: as the exemplary adapters were designed for ligation to end-repaired, dA-tailed templates, the adapter mix may be used in an equivalent way to any other Illumina adapters as will be apparent to those skilled in the art of NGS. In the proposed expriments, a KAPA HyperPlus kit was used and 5 μl of 15 μM adapters were added to the ligation mix.

PCR: The purified, adapter-ligated DNA template was used as input to PCR steps as follow:

First Mix, Per Sample:
  10 μl KAPA HiFi buffer
  10.5 μl H$_2$O
  0.75 μl dA/C/GTP mix (20 mM each)
  1 μl KAPA HiFi
  2.5 μl PE1_SG2_MM_MPX primer (20 μM)
  2.5 μl SG2.4-Block (20 μM)
  20 μl template in IDTE or water Program for Part 1:
  −72° C.-10 s
  98° C.-30 s
  48° C.-1 min
  Then. bring to 20° C.

During this short program, another set of tubes were prepared, each containing, per sample:
  2.5 μl PE2_MPX (20 μM)
  0.75 μl dTTP (20 mM)

The tubes containing the first PCR mix were taken out of the thermocycler and their contents added to the second set of tubes with primer 2 and dTTP. The resulting solution was mixed by pipetting and spin down. The tubes were put back into the thermocycler and the second part of the program was run as follows:

Program for Part II:
  72° C.-30 s
  Iterate n* cycles of:
  98° C.-15 s
  60° C.-30 s
  72° C.-30 s
  end cycle
  72° C.-1 min FIG. 9 shows a minimum of 450 ng as the resulting amount of DNA produced according to the above protocol in a first experiment for three different samples with 11 cycles of PCR. FIG. 10 shows the Bioanalyzer trace for sample 2 after the pre-capture PCR, showing the size distribution.

Sequencing: An Illumina NextSeq500 sequencer was then used to read the amplified DNA sequences. FIG. 11 and FIG. 12 respectively show evidence of the resulting sequencing and mapping quality distribution for a typical sample.

Finally, FIG. 13 shows a screen capture of the IGV (Integrated Genomics Viewer-https://software.broadinstitute.org/software/igv/) software showing the resulting genomic datasets after alignment with the Burrow-Wheeler Aligner bwa (http://bio-bwa.sourceforge.net/). After alignment, it is thus possible to discriminate between four DNA fragments of interest (labeled 1,2,3 and 4). Fragments 1-3 come from the same molecule (1-2 from the plus strand and 3 from the minus strand), while fragment 4 comes from a different molecule.

The present disclosure may be embodied in other specific forms without departing from its spirit or essential characteristics. The described embodiments are to be considered in all respects only as illustrative and not restrictive.

The invention claimed is:

1. A method for generating one or more DNA products comprising a first and second index sequence (IS), the first and second ISs having different nucleotide sequences and allowing for identification of the source of a PCR sample, said method comprising:
   (I) ligating, in a reaction mixture, a first adaptor comprising a first strand identifier sequence (SIS) and a primering sequence-binding region to one end of a double-stranded DNA having two ends, and a second adaptor comprising a second SIS and a primering sequence-binding region to the other end of the double-stranded DNA, the first and second SISs having different nucleotide sequences, to obtain an adapted double-stranded DNA having a single-stranded 5' overhang at each end;
   (II) denaturing the adapted double-stranded DNA to obtain at least one single-stranded DNA template in the presence of a first primering sequence (PS) and a blocking oligonucleotide;
   (III) decreasing the temperature under conditions that promote: (A) annealing of (i) the blocking oligonucleotide and (ii) the first PS comprising a first index sequence (IS) to the at least one single-stranded template, wherein (i) the blocking oligonucleotide and (ii) the first PS anneal to a first primering sequence-binding region of the at least one single-stranded template, the blocking oligonucleotide having an annealing temperature to the single-stranded template equal to or higher than the annealing temperature of the first PS;
   (IV) without changing the temperature, adding to the reaction mixture a second PS comprising a second IS;
   (V) incubating at a temperature that allows the blocking oligonucleotide to detach from the at least one single-stranded template and elongation from the first PS to proceed;
   (VI) denaturing to obtain at least one single-stranded DNA comprising the first IS; and
   (VII) incubating under conditions that promote annealing of the second PS to the at least one single-stranded DNA comprising the first IS, wherein the second PS anneal to a second primering sequence-binding region of the at least one single-stranded DNA and subsequent DNA polymerization to obtain one or more DNA products comprising a first and second IS, the first and second ISs having different nucleotide sequences.

2. The method according to claim 1, wherein the ligating in (I) proceeds at a temperature of 12-25° C.

3. The method according to claim 1, wherein the denaturing in (II) proceeds at a temperature of 85-105° C.

4. The method according to claim 1, wherein temperature at which the blocking oligonucleotide anneals to the single-stranded template in (III) is in the range of 44-52° C.

5. The method according to claim 1, wherein the temperature that allows the blocking oligonucleotide to detach from the single-stranded template and elongation from the second PS to proceed in (V) is in the range of 60-75° C.

6. The method according to claim 1, wherein the denaturing in (VI) proceeds at a temperature of 85-105° C.

7. The method according to claim 1, wherein the conditions that promote annealing of the second PS to the at least one single-stranded DNA comprising the first IS and subsequent DNA polymerization in (VII) comprise incubating at a temperature higher than the annealing temperature at which the blocking oligonucleotide anneals to the at least one single-stranded template.

8. The method according to claim 7, wherein the temperature higher than the annealing temperature at which the blocking oligonucleotide anneals to the at least one single-stranded template is in the range of 57-65° C.

9. The method according to claim 1, which comprises performing (I)-(III) in a reaction mixture lacking at least one of dATP, dTTP, dCTG, or dGTP, with the proviso that when dTTP is lacking dUTP is also lacking.

10. The method according to claim 9, which further comprises adding to the reaction mixture in (IV) the dNTP or dNTPs lacking in (I)-(III).

11. The method according to claim 1, which comprises partially elongating the adapted double-stranded DNA in the presence of a dNTP mixture lacking at least one of dATP, dTTP, dCTG, or dGTP, with the proviso that when dTTP is lacking dUTP is also lacking, wherein the partial elongation occurs after the ligating in (I).

* * * * *

SEQUENCE LISTING

```
<160> NUMBER OF SEQ ID NOS: 7

<210> SEQ ID NO 1
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (33)..(38)
<223> OTHER INFORMATION: n is a, c, g, or t
<220> FEATURE:
<221> NAME/KEY: misc_feature
<222> LOCATION: (46)..(47)
<223> OTHER INFORMATION: Phosphorothioate bound

<400> SEQUENCE: 1
gactggagtt cagacgtgag ctcttccgtt ctnnnnnngc caatgct          47

<210> SEQ ID NO 2
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (33)..(38)
<223> OTHER INFORMATION: n is a, c, g, or t
<220> FEATURE:
<221> NAME/KEY: misc_feature
<222> LOCATION: (46)..(47)
<223> OTHER INFORMATION: Phosphorothioate bound

<400> SEQUENCE: 2
gactggagtt cagacgtgag ctcttccgtt ctnnnnnntc actgcgt          47
```

```
<210> SEQ ID NO 3
<211> LENGTH: 70
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (69)..(70)
<223> OTHER INFORMATION: Phosphorothioate bound

<400> SEQUENCE: 3
aatgatacgg cgaccaccga gatctacaca ggcgaagaca ctctttccct acacgacgct    60
cttccgttct                                                          70

<210> SEQ ID NO 4
<211> LENGTH: 70
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (69)..(70)
<223> OTHER INFORMATION: Phosphorothioate bound

<400> SEQUENCE: 4
aatgatacgg cgaccaccga gatctacact aatcttaaca ctctttccct acacgacgct    60
cttccgttct                                                          70

<210> SEQ ID NO 5
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (65)..(66)
<223> OTHER INFORMATION: Phosphorothioate bound

<400> SEQUENCE: 5
caagcagaag acggcatacg agattaatgc gcgtgactgg agttcagacg tgtgctcttc    60
cgatct                                                              66

<210> SEQ ID NO 6
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (65)..(66)
<223> OTHER INFORMATION: Phosphorothioate bound

<400> SEQUENCE: 6
caagcagaag acggcatacg agatcggcta tggtgactgg agttcagacg tgtgctcttc    60
cgatct                                                              66

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (19)..()
<223> OTHER INFORMATION: Inverted dT at the 3' end

<400> SEQUENCE: 7
cggaagagct cacgtctgt                                              19
```